US008101804B2

(12) United States Patent
Schouteeten et al.

(10) Patent No.: US 8,101,804 B2
(45) Date of Patent: Jan. 24, 2012

(54) PROCESS FOR THE SYNTHESIS OF (E)-STILBENE DERIVATIVES WHICH MAKES IT POSSIBLE TO OBTAIN RESVERATROL AND PICEATANNOL

(75) Inventors: Alain Schouteeten, Ezanville (FR); Sébastien Jus, Paris (FR); Jean-Claude Vallejos, La Ciotat (FR)

(73) Assignee: Clariant Specialty Fine Chemicals (France), Trosly Breuil (FR)

( * ) Notice: Subject to any disclaimer, the term of this patent is extended or adjusted under 35 U.S.C. 154(b) by 245 days.

(21) Appl. No.: 12/375,507

(22) PCT Filed: Jul. 25, 2007

(86) PCT No.: PCT/EP2007/057650
§ 371 (c)(1),
(2), (4) Date: Mar. 25, 2009

(87) PCT Pub. No.: WO2008/012321
PCT Pub. Date: Jan. 31, 2008

(65) Prior Publication Data
US 2010/0004483 A1 Jan. 7, 2010

(30) Foreign Application Priority Data
Jul. 28, 2006 (FR) ...................................... 06 53178

(51) Int. Cl.
*C07C 45/41* (2006.01)
*C07C 33/28* (2006.01)
*C07C 69/00* (2006.01)
*C07C 313/18* (2006.01)
*C07C 59/215* (2006.01)

(52) U.S. Cl. ........ 568/309; 562/470; 564/102; 564/251; 568/331; 568/644; 568/645; 568/646; 568/807; 568/811; 568/813; 560/53

(58) Field of Classification Search .................... None
See application file for complete search history.

(56) References Cited

U.S. PATENT DOCUMENTS 2,537,950 A * 1/1951 Allen ............................ 564/305
3,767,289 A * 10/1973 Aviram et al. ................ 349/186
6,407,142 B1 6/2002 Courbriere et al.

FOREIGN PATENT DOCUMENTS

| EP | 1 466 884 | 10/2004 |
| EP | 1884508 | 2/2008 |
| WO | WO 00/69430 | 11/2000 |
| WO | WO 01/60774 | 8/2001 |
| WO | WO 03/086414 | 10/2003 |
| WO | WO 2005/023740 | 3/2005 |
| WO | WO 2005/069998 | 8/2005 |

OTHER PUBLICATIONS

Mannila et al., Liebigs Annalen der Chemie, Sep. 1993, vol. 9, pp. 1037-1039, CAPLUS abstract only.*
English Abstract for EP 1 466 884.
Journal of Medicinal Chemistry, 30(11), (1987), pp. 2121-2126.
Tetrahedron, 59(18), (2003), pp. 3315-3321.
Chemistry Letters, 11, (1999), pp. 1193-1194.
Journal of the American Chemical Society, 126(32), (2004), pp. 9882-9883.
Chemistry and Pharmaceutical Bulletin, (1992), 40(10), pp. 2842-2844.
Journal of Organic Chemistry, (2002), 67, pp. 4627-4629.
Advanced Organic Chemistry, Reactions, Mechanisms and Structure, John Wiley & Sons, 4th edition, pp. 491-493, Nov. 1998.
Advanced Organic Chemistry, Reactions, Mechanisms and Structure, John Wiley & Sons, 4th edition, p. 629, Nov. 1998.
Advanced Organic Chemistry, Reactions, Mechanisms and Structure, John Wiley & Sons, 4th edition, pp. 910-918, Nov. 1998.
Advanced Organic Chemistry, Reactions, Mechanisms and Structure, John Wiley & Sons, 4th edition, pp. 1019-1021, Nov. 1998.
Roberts, et al., Canadian Journal of Chemistry, (81), (2003), pp. 709-722.
Talvitie, et al., Acta Chemica Scandinavia, (50), (1996), pp. 1143-1146.
International Search Report and Written Opinion of the International Searching Authority for PCT/EP2007/057650, Apr. 2005.
INPI Preliminary Search Report for FR0653178, dated Mar. 30, 2007.
Extended European Search for EP 09 01 5839, dated Aug. 2, 2010.

* cited by examiner

*Primary Examiner* — Rosalynd Keys
(74) *Attorney, Agent, or Firm* — Tod A. Waldrop

(57) ABSTRACT

A subject-matter of the present invention is a novel process for the synthesis of (E)-stilbene derivatives targeted at obtaining in particular resveratrol and piceatannol.

24 Claims, 1 Drawing Sheet

Figure 1:
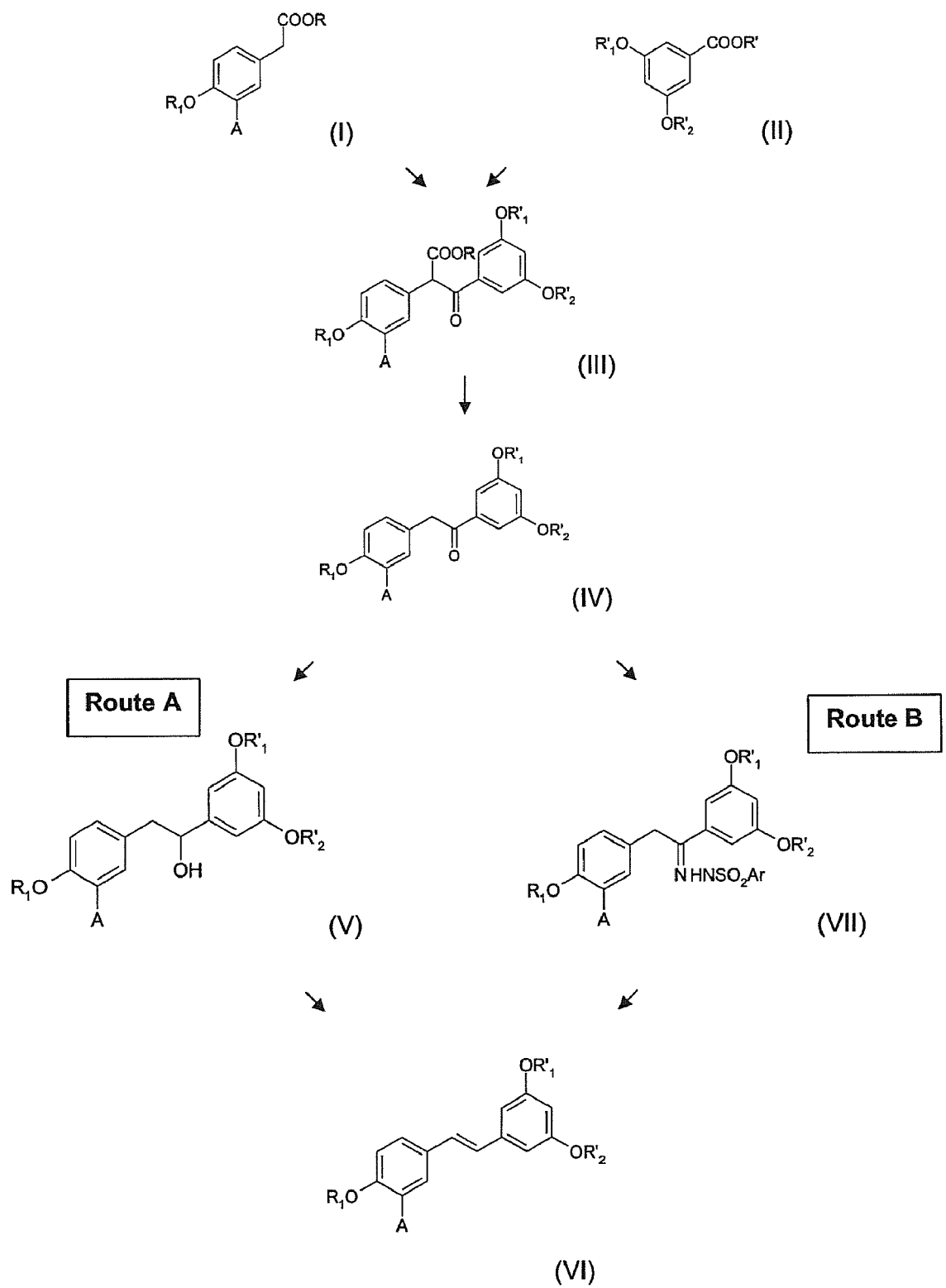

PROCESS FOR THE SYNTHESIS OF (E)-STILBENE DERIVATIVES WHICH MAKES IT POSSIBLE TO OBTAIN RESVERATROL AND PICEATANNOL

A subject-matter of the present invention is a novel process for the synthesis of (E)-stilbene derivatives targeted in particular at obtaining resveratrol and piceatannol.

The invention relates more particularly to a process for the synthesis of (E)-stilbene derivatives of formula (VI) as defined in the present patent application, in particular (E)-trimethylresveratrol, (E)-tribenzylresveratrol and (E)-tetramethylpiceatannol, which make it possible to obtain resveratrol and piceatannol.

Polyhydroxystilbenes are compounds which are found in various plants and which have received particular attention as they exhibit a great variety of therapeutic properties.

These derivatives include resveratrol ((E)-3,5,4'-trihydroxystilbene) and piceatannol ((E)-3,5,3',4'-tetrahydroxystilbene) of formulae:

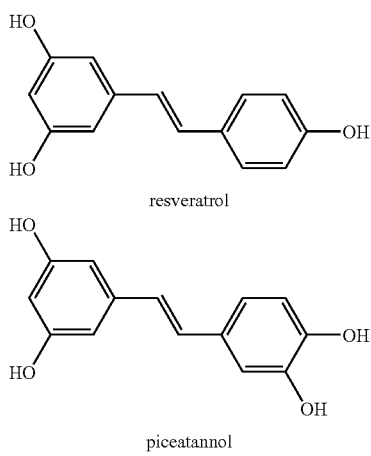

resveratrol piceatannol

Resveratrol and piceatannol are compounds belonging to the class of the polyphenols, known for exerting antioxidant effects capable of preventing or delaying the deleterious effects of oxidative stress.

In the therapeutic field, resveratrol is listed as platelet anti-aggregant, anti-inflammatory or vasodilator or as cell proliferation inhibitor.

These products have resulted in the development of numerous synthetic routes but the latter are not satisfactory from an industrial viewpoint.

The synthetic routes envisaged require, in the majority of cases, the protection of the phenolic functional groups, either in the form of ether derivatives (generally methyl, isopropyl, benzyl or silyl derivatives) or in the form of ester derivatives (generally acetyl or benzoyl derivatives), and the polyhydroxystilbenes are subsequently obtained by release of the said functional groups by known methods.

The most widely used route for obtaining resveratrol or piceatannol is described in numerous publications and patent applications, including the following: EP 1 466 884; WO 2003/086414. It consists in condensing, according to "Wittig" or "Wittig-Horner" conditions, a protected hydroxyaromatic (or polyhydroxyaromatic) aldehyde, such as protected 3,5-dihydroxybenzaldehyde, with a phosphonium salt or a phosphonate, such as protected 4-hydroxybenzyltriphenylphosphonium bromide.

However, Wittig or Wittig-Horner reactions generally result in a mixture of (E) and (Z)-stilbene isomers which are difficult to separate, which requires an additional stage in order to convert the undersirable Z isomer to the E isomer, either with catalytic iodine, as disclosed in US 2004/00115020, or else by reaction with a diaryl disulphide, as described in Chem. Pharm. Bull., (1992), 40(10), 2842-2844. This additional stage results in such cases in the formation of by-products, which requires a difficult purification stage which is not very desirable industrially. The conversion of the Z isomer to the E isomer can be obtained by reaction of the Z isomer with a palladium(II) complex, as described in J. Org. Chem., (2002), 67, 4627-4629. However, the large amount of the said complex to be employed [20 mol % of $(MeCN)_2PdCl_2$] renders the process very expensive.

Another conventional route for obtaining resveratrol or piceatannol consists in obtaining an α-phenylcinnamic acid by the Perkin reaction, as disclosed in WO 2000/69430 and Tetrahedron, 59, (2003), 3315-21, by reacting a hydroxy- (or polyhydroxy)phenylacetic acid (or an ether/ester derivative) with a (protected or unprotected) hydroxy- (or polyhydroxy) aromatic aldehyde. The decarboxylation of the cinnamic derivative (Cu/quinoline at 260° C.) then results in the stilbene derivative.

However, the latter reaction requires severe conditions (high temperature, polluting metal catalyst) for the decarboxylation and generally results in the predominant (Z) isomer, which requires an additional isomerization stage.

Another route for the synthesis of resveratrol and piceatannol uses reactions of Heck type, such as the condensation of 3,5-diacetoxystyrene with 4-acetoxybromobenzene, as is disclosed in WO 2005/023740, or else the condensation of 4-acetoxystyrene with 3,5-dimethoxybenzoyl chloride, as indicated in WO 2001/60774, or else again the condensation with 3,5-diacetoxybenzoyl chloride disclosed in WO 2005/069998.

However, these reactions require the use of starting materials which are difficult to obtain, such as 3,5-diacetoxystyrene, and also catalysts based on palladium salts which are expensive and not very stable under the reaction conditions required, which result in low and variable yields.

In order to solve the disadvantages of the abovementioned synthetic routes and to reduce the cost for the production of resveratrol and piceatannol, the inventors have developed an alternative route for the synthesis of polyhydroxystilbenes.

This novel route consists in obtaining (E)-stilbene derivatives from 1,2-diarylethanone derivatives.

The (E)-stilbene derivatives obtained are isomers of E type which are subsequently deprotected to give the products of interest, such as, for example resveratrol or piceatannol.

This novel synthetic route exhibits the advantage, in addition to dispensing with the stage of separation of the E and Z isomers which presented a problem in the prior art, of using, as starting materials, 1,2-diarylethanone derivatives which can be obtained at low cost from reactants such as hydroxyaromatic acids, optionally etherified, and hydroxyaromatic esters.

FIG. 1 illustrates the novel route for the synthesis of polyhydroxystilbenes disclosed in the present patent application.

A first subject-matter of the present application is thus a process for the synthesis of an (E)-stilbene derivative of formula (VI)

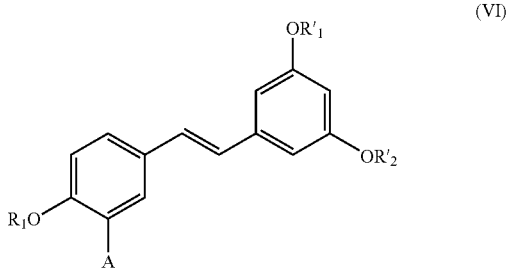

in which

A represents hydrogen or an OR$_2$ group, and

R$_1$, R$_2$, R'$_1$ and R'$_2$ represent, independently of one another, a linear or branched alkyl group comprising from 1 to 6 carbon atoms or an aralkyl group including from 7 to 16 carbon atoms which is optionally substituted by one or more alkoxy or halogen groups, it also being possible for R$_1$ and R$_2$ to form a hydrocarbon chain of structure —(CH$_2$)$_n$— with n=1 to 3, characterized in that a 1,2-diarylethanone compound of formula (IV)

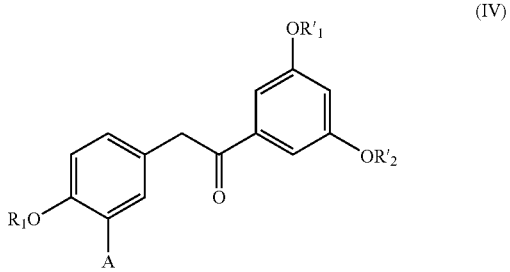

in which

A represents hydrogen or an OR$_2$ group, and

R$_1$, R$_2$, R'$_1$ and R'$_2$ represent, independently of one another, a linear or branched alkyl group comprising from 1 to 6 carbon atoms or an aralkyl group including from 7 to 16 carbon atoms which is optionally substituted by one or more alkoxy or halogen groups, R$_1$ it also being possible for and R$_2$ to form a hydrocarbon chain of structure —(CH$_2$)$_n$— with n=1 to 3;

is reacted as synthetic intermediate.

In the present invention and what follows, where R$_1$, R$_2$, R'$_1$ and R'$_2$ represent, independently of one another, a linear or branched alkyl group comprising from 1 to 6 carbon atoms, it is, for example, a methyl, ethyl, propyl, isopropyl, butyl, isobutyl, sec-butyl, tert-butyl, pentyl or hexyl group. When R$_1$, R$_2$, R'$_1$ and R'$_2$ represent an aralkyl group including from 7 to 16 carbon atoms, it is, for example, a benzyl, 1-phenylethyl, naphthylmethyl or 1-naphthylethyl group.

In the present invention and in what follows, as regards the substituents, the term "alkoxy" denotes, for example, a methoxy, ethoxy, propoxy or butoxy radical.

The halogen radical means Cl, Br, F or I.

A preferred aspect of the invention consists in synthesizing the following (E)-stilbene derivatives of formula (VI):

(E)-trimethylresveratrol, in which A represents a hydrogen atom, R$_1$, R'$_1$ and R'$_2$ being methyl groups or (E)-tribenzylresveratrol, in which A represents a hydrogen atom, R$_1$, R'$_1$ and R'$_2$ being benzyl groups, for the purpose of obtaining resveratrol, and (E)-tetramethylpiceatannol, in which A represents —OCH$_3$, R$_1$, R'$_1$ and R'$_2$ being methyl groups, for the purpose of obtaining piceatannol.

Such products of formula (VI) are described in the literature.

The intermediates of formula (IV), in which A represents hydrogen and R$_1$, R'$_1$ and R'$_2$ each represent a benzyl group or in which A represents an —OCH$_3$ group and R$_1$, R'$_1$ and R'$_2$ each represent a methyl group or in which A represents hydrogen, R'$_1$ and R'$_2$ represent a methyl group and R$_1$ represents an isopropyl group or in which A represents an —OR$_2$ group, R'$_1$ and R'$_2$ represent a methyl group and R$_1$ and R$_2$ form a hydrocarbon chain of structure —(CH$_2$)$_n$— with n=1 are novel products which represent a further subject-matter of the invention.

These novel compounds of formula (IV) consist in particular of the following:

1-(3,5-dibenzyloxyphenyl)-2-(4-benzyloxyphenyl)ethanone (or 3,5,4'-tribenzyloxydeoxybenzoin);

1-(3,5-dimethoxyphenyl)-2-(3,4-dimethoxyphenyl)ethanone (or 3,5,3',4'-tetramethoxydeoxybenzoin);

1-(3,5-dimethoxyphenyl)-2-(4-isopropyloxyphenyl)ethanone, and 1-(3,5-dimethoxyphenyl)-2-(3,4-methylenedioxyphenyl)ethanone which are of use respectively in the manufacture of the following derivatives of formula (VI):

(E)-tribenzylresveratrol, which makes it possible, during the stage described later, to obtain resveratrol;

(E)-tetramethylpiceatannol, which makes it possible, during the stage described later, to obtain piceatannol;

(E)-3,5-dimethoxy-4'-isopropyloxy-stilbene, and (E)-3,5-dimethoxy-3',4'-methylenedioxy-stilbene.

Another preferred aspect of the invention consists in synthesizing (E)-trimethylresveratrol (compound of formula (VI)) from the compound of formula (IV) 1-(3,5-dimethoxyphenyl)-2-(4-methoxyphenyl)ethanone (or 3,5,4'-trimethoxydeoxybenzoin).

The compound of formula (IV) can be used in two different ways to obtain the (E)-stilbene derivative of formula (VI) which is at the heart of the present invention:

either by reducing the compound of formula (IV) to give an alcohol of formula (V) and by then dehydrating the alcohol formed (route A);

or by synthesis of arylsulphonylhydrazone compounds, by reacting the compound of formula (IV) with an arylsulphonylhydrazide, and by then reacting the arylsulphonylhydrazones formed with a base (route B).

Synthesis of the 1,2-diarylethanones of Formula (IV)

The 1,2-diarylethanones of formula (IV) used in the process according to the invention are preferably obtained by a decarboxylation reaction starting from β-ketoesters of formula (III)

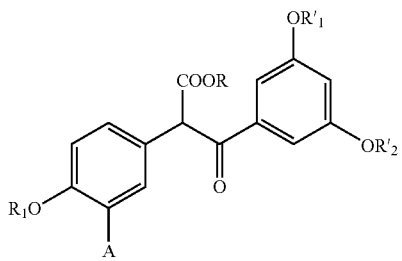

(III)

in which
A represents hydrogen or else an $OR_2$ group,
$R_1, R_2, R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups,
it also being possible for $R_1$ and $R_2$ to form a hydrocarbon chain of structure —$(CH_2)_n$— with n=1 to 3,
R is a linear or branched alkyl group comprising from 1 to 6 carbon atoms.

In the present invention and in what follows, when R represents a linear or branched alkyl group comprising from 1 to 6 carbon atoms, it is, for example, a methyl, ethyl, propyl, isopropyl, butyl, isobutyl, sec-butyl, tert-butyl, pentyl or hexyl group.

The reaction for the decarboxylation of the β-ketoesters of formula (III) to give ketones of structure (IV) can be carried out under acidic conditions in the presence, for example, of acid/solvent pairs, such as the following concentrated hydrochloric acid/acetic acid, concentrated hydrochloric acid/ethanol or sulphuric acid/acetic acid, or else without solvent, in the presence of boric acid or anhydride, as indicated in Advanced Organic Chemistry, Reactions, Mechanisms and Structure, John Wiley & Sons, 4th edition, page 629.

Preferably, the decarboxylation reaction is carried out without solvent in the presence of 1 to 5 equivalents of boric acid or of boric anhydride at a temperature of between 100 and 180° C., more preferably in the presence of 1 to 2 equivalents of boric acid or more preferably still with 1 equivalent of boric acid.

The present invention provides, to this end, novel compounds of formula (III) in which
R represents a methyl group, and
either A represents hydrogen and the $R_1, R'_1$ and $R'_2$ groups represent methyl groups or benzyl groups,
or A represents an —$OCH_3$ group and the $R_1, R'_1$ and $R'_2$ groups each represent a methyl group,
or A represents hydrogen, $R'_1$ and $R'_2$ represent a methyl group and $R_1$ represents an isopropyl group,
or A represents an —$OR_2$ group, $R'_1$ and $R'_2$ represent a methyl group and $R_1$ and $R_2$ form a hydrocarbon chain of structure —$(CH_2)_n$— with n=1;
consisting in particular of the following compounds:
methyl 3-(3,5-dimethoxyphenyl)-2-(4-methoxyphenyl)-3-oxopropionate;
methyl 3-(3,5-dibenzyloxyphenyl)-2-(4-benzyloxyphenyl)-3-oxopropionate;
methyl 3-(3,5-dimethoxyphenyl)-2-(3,4-dimethoxyphenyl)-3-oxopropionate;
methyl 3-(3,5-dimethoxyphenyl)-2-(4-isopropyloxyphenyl)-3-oxopropionate;
methyl 3-(3,5-dimethoxyphenyl)-2-(3,4-methylenedioxyphenyl-3-oxopropionate;
which compounds make it possible to respectively obtain the following compounds of formula (IV):
1-(3,5-dimethoxyphenyl)-2-(4-methoxyphenyl)ethanone;
1-(3,5-dibenzyloxyphenyl)-2-(4-benzyloxyphenyl)ethanone;
1-(3,5-dimethoxyphenyl)-2-(3,4-dimethoxyphenyl)ethanone;
1-(3,5-dimethoxyphenyl)-2-(4-isopropyloxyphenyl)ethanone; and
1-(3,5-dimethoxyphenyl)-2-(3,4-methylenedioxyphenyl)ethanone;
of use respectively in producing (E)-trimethylresveratrol, (E)-tribenzylresveratrol, (E)-tetramethylpiceatannol, (E)-3,5-dimethoxy-4'-isopropyloxy-stilbene and (E)-3,5-dimethoxy-3',4'-methylenedioxy-stilbene.

The β-ketoesters of formula (III) can be obtained, preferably, by a condensation reaction of Claisen type between ether/ester derivatives (I) and ether/ester derivatives (II), such as described, for example, in Advanced Organic Chemistry, Reactions, Mechanisms and Structure, John Wiley & Sons, 4th edition, pages 491-493, as indicated below:

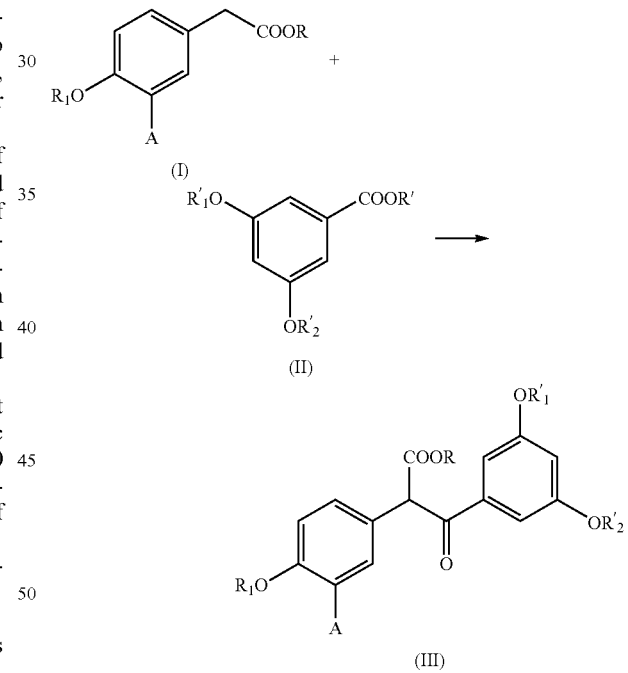

In the formulae (I) and (II),
A represents hydrogen or else an $OR_2$ group,
$R_1, R_2, R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups,
it also being possible for $R_1$ and $R_2$ to form a hydrocarbon chain of structure —$(CH_2)_n$— with n=1 to 3, and
R and R' represent, independently of one another, a linear or branched alkyl group comprising from 1 to 6 carbon atoms.

In the present invention, where R' represents a linear or branched alkyl group comprising from 1 to 6 carbon atoms, it is, for example, a methyl, ethyl, propyl, isopropyl, butyl, isobutyl, sec-butyl, tert-butyl, pentyl or hexyl group.

This condensation reaction is generally carried out in the presence of a strong base at the reflux temperature of the reaction medium with stoichiometric amounts of ether/ester derivatives (I) and (II).

Mention may be made, as examples of strong base, of alkali metal alkoxides, such as sodium ethoxide, or alkali metal hydrides, such as sodium hydride.

Under preferred conditions of implementation of the process described above, 2 to 5 equivalents of strong base are employed, particularly 2 to 2.5 equivalents.

The starting ether/esters (I) and (II) can be synthesized from the corresponding hydroxyaromatic acids, hydroxyaromatic esters or etherified hydroxyaromatic acids by known methods, such as described in *J. Med. Chem.*, 30(11), (1987), 2121-26; *Tetrahedron*, 59, (2003), 3315-22; *Chem. Lett.*, 11, (1999), 1193-94; *J. Am. Chem. Soc.*, 126(32), (2004), 9882-83. These starting materials are inexpensive reactants which are easy to employ for a person skilled in the art.

4-hydroxyphenylacetic acid, resorcylic acid or 3,4-dihydroxyphenylacetic acid can be cited as examples of hydroxyaromatic acids.

Route A for the Synthesis of the Compounds of Formula (VI)

This route consists of the reduction of the ketones of formula (IV) described above in order to obtain 1,2-diarylethanol derivatives of formula (V) as indicated below:

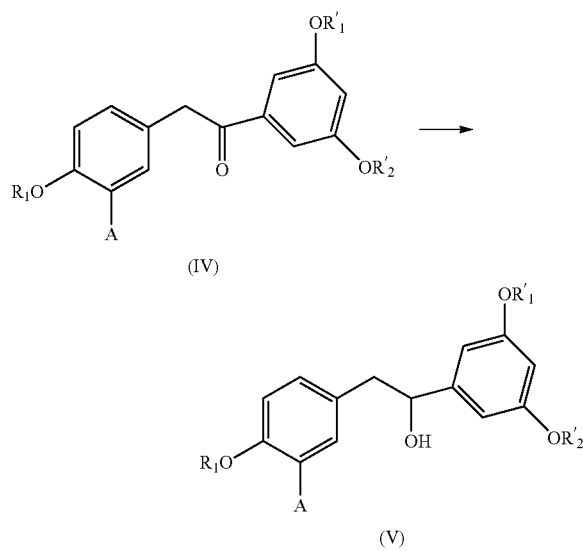

in which

A represents hydrogen or else an $OR_2$ group, $R_1$, $R_2$, $R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups, it also being possible for $R_1$ and $R_2$ to form a hydrocarbon chain of structure —$(CH_2)_n$— with n=1 to 3.

The ketones of formula (IV) can be reduced by application or adaptation of the methods described, for example, in Advanced Organic Chemistry, Reactions, Mechanisms and Structure, John Wiley & Sons, 4th edition, pages 910-918.

Under preferred conditions of the process described above, the ketones of formula (IV) are reduced to give alcohols of formula (V) by the action of a metal hydride, such as $LiAlH_4$ or $NaBH_4$. This reduction is generally carried out using from 0.25 to 3 equivalents of metal hydride. Particularly, 1 equivalent of $NaBH_4$ can be used.

Alternatively, for the ketones of formula (IV) in which A represents hydrogen or else an $OR_2$ group and $R_1$, $R_2$, $R'_1$ and $R'_2$ represent, independently of one another, a linear or branched alkyl group comprising from 1 to 6 carbon atoms, it also being possible for $R_1$ and $R_2$ to form a hydrocarbon chain of structure —$(CH_2)_n$— with n=1 to 3, the reduction can be carried out by hydrogenation. Under preferred conditions, the hydrogenation is carried out in the presence of catalysts, such as Pd/C, in a solvent, such as methanol or ethanol, under a hydrogen pressure of the order of $3\times10^5$ Pa (3 bar) to $50\times10^5$ Pa (50 bar), at a temperature of between ambient temperature and approximately 50° C. Particularly, the said hydrogenation reaction is carried out under a hydrogen pressure of between $5\times10^5$ Pa and $10\times10^5$ Pa, at ambient temperature, in the presence of 5 to 20% by weight of Pd/C with respect to the ketone of formula (IV).

This reaction makes it possible in particular to obtain the following preferred compounds of formula (V):

1-(3,5-dimethoxyphenyl)-2-(4-methoxyphenyl)ethanol, and 1-(3,5-dimethoxyphenyl)-2-(3,4-dimethoxyphenyl)ethanol and more particularly a novel compound of formula (V) in which A represents hydrogen and $R_1$, $R'_1$ and $R'_2$ represent a benzyl group, consisting in particular of 1-(3,5-dibenzyloxyphenyl)-2-(4-benzyloxyphenyl)ethanol. This novel compound is obtained by reacting the compound of formula (IV) 1-(3,5-dibenzyloxyphenyl)-2-(4-benzyloxyphenyl)ethanone as indicated above.

Once the alcohols of structure (V) are formed, the latter are dehydrated in the presence of catalytic amounts of strong acid, such as, for example, sulphuric acid, p-toluenesulphonic acid or phosphoric acid.

Preferably, the dehydration reaction is carried out in an aromatic solvent, such as toluene, at reflux, in the presence of catalytic amounts of p-toluenesulphonic acid of 1 to 20 mol % with respect to the alcohol of formula (V) and more preferably of 5 to 10 mol %. The water formed during the reaction is generally removed by azeotropic distillation. The (E)-stilbene derivatives of structure (VI) of the invention are obtained according to this procedure.

Route B for the Synthesis of the Compounds of Formula (VI)

This other route consists, in a first step, in synthesizing arylsulphonylhydrazone compounds of formula (VII) by reacting the compound of formula (IV) with an arylsulphonylhydrazide, as indicated in the following scheme:

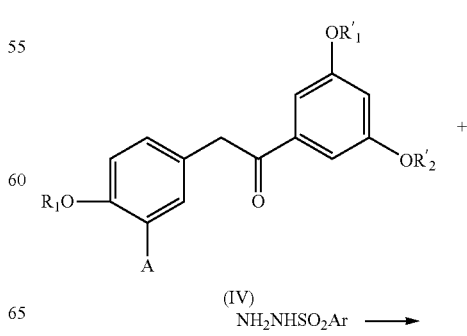

-continued

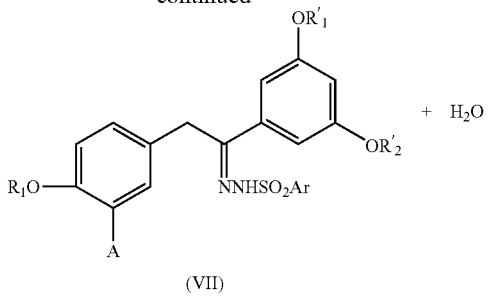

This reaction is generally carried out in an alcoholic solvent, such as methanol or ethanol, or in an aromatic solvent, such as toluene, in the presence of catalytic amounts of acid, such as sulphuric acid or hydrochloric acid, if necessary.

The arylsulphonylhydrazide compounds are known from the literature or are commercially available. Mention may be made, by way of examples, of phenylsulphonylhydrazide and p-toluenesulphonylhydrazide, sold by Aldrich.

Under preferred conditions, this reaction is carried out at reflux in ethanol or toluene using an excess of arylsulphonylhydrazide of between 1.1 and 1.5 equivalents. p-Toluenesulphonylhydrazide is preferred.

The compounds of formula (VII)

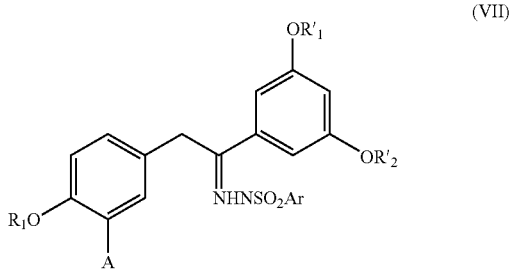

thus synthesized are characterized in that:
Ar represents a phenyl or o-, m- or p-tolyl group,
A represents hydrogen or else an $OR_2$ group,
$R_1$, $R_2$, $R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups, it also being possible for $R_1$ and $R_2$ to form a hydrocarbon chain of structure —$(CH_2)_n$— with n=1 to 3.

In particular, the present invention provides novel compounds of formula (VII), characterized in that:
Ar represents a p-tolyl group, and
either A represents hydrogen and all three of the $R_1$, $R'_1$ and $R'_2$ groups represent methyl groups or benzyl groups,
or A represents an —$OCH_3$ group and the $R_1$, $R'_1$ and $R'_2$ groups each represent a methyl group,
or A represents hydrogen, $R'_1$ and $R'_2$ represent a methyl group and $R_1$ represents an isopropyl group,
or A represents an —$OR_2$ group, $R'_1$ and $R'_2$ represent a methyl group and $R_1$ and $R_2$ form a hydrocarbon chain of structure —$(CH_2)_n$— with n=1.

These novel compounds consist in particular of the following:
N-[1-(3,5-dimethoxyphenyl)-2-(4-methoxyphenyl)ethylidene]-N'-tosylhydrazine,
N-[1-(3,5-dibenzyloxyphenyl)-2-(4-benzyloxyphenyl)ethylidene]-N'-tosylhydrazine and,
N-[1-(3,5-dimethoxyphenyl)-2-(4-isopropyloxyphenyl)ethylidene]-N'-tosylhydrazine;
which compounds are particularly of use in obtaining resveratrol according to the invention, and
N-[1-(3,5-dimethoxyphenyl)-2-(3,4-dimethoxyphenyl)ethylidene]-N'-tosylhydrazine and,
N-[1-(3,5-dimethoxyphenyl)-2-(3,4-methylenedioxyphenyl)ethylidene]-N'-tosylhydrazine;
which are particularly of use in obtaining piceatannol according to the invention.

According to the process of the invention, in a second step, the arylsulphonylhydrazones of structure (VII) are reacted under "Shapiro" or "Bamford-Stevens" conditions by application or adaptation of the methods described, for example, in Organic Chemistry, Reactions, Mechanisms and Structure, John Wiley & Sons, 4th edition, pages 1019-1021.

The reaction is generally carried out in a solvent in the presence of a base and in the presence of catalytic amounts of phase transfer catalyst or of surfactant, if these are necessary.

Under preferred conditions of implementation of the process described above, use is made of an excess of strong base of between 2 to 3 equivalents, such as lithium derivatives, for example methyllithium ethyllithium, butyllithium or lithium diisopropylamide, in nonhydroxylated solvents, such as diethyl ether, isopropyl ether, methyl tert-butyl ether, THF or dioxane, at a temperature of between 0° C. and 5° C.

Under other preferred conditions, use is made of at least one equivalent of strong base, more preferably of an excess of strong base of between 2 to 5 equivalents, such as alkali metal alkoxides, such as sodium methoxide, potassium tert-butoxide or sodium amide, or alkali metal hydrides, such as sodium hydride or potassium hydride, or alkaline bases, such as sodium or potassium hydroxide, or sodium or potassium carbonate, at the reflux temperature of the reaction medium, in hydroxylated or nonhydroxylated solvents, preferably nonhydroxylated solvents, having a boiling point of at least 90° C., preferably of at least 100° C., such as aromatic solvents, for example toluene, xylenes, mesitylene, ethylbenzene or chlorobenzene, dioxane or ethylene glycol, or in glycol ethers with a boiling point of at least 100° C.

Use may be made, to promote the dissolution of the bases in the reaction medium, of phase transfer catalysts, such as quaternary ammonium salts, for example triethylbenzylammonium chloride, or polyglycol ethers, for example Triton X100®.

Under yet other preferred conditions, the reaction is carried out in a nonhydroxylated solvent having a boiling point of at least 100° C. at the reflux temperature of the reaction medium, in the presence of 2.1 to 2.2 equivalents of potassium tert-butoxide and in the presence of 1 to 10 mol % of Triton X100® with respect to the arylsulphonylhydrazone of formula (VII).

(E)-stilbene derivatives of formula (VI) as defined above are thus obtained and can be converted to polyhydroxystilbenes as described later.

In particular, the present invention provides a novel compound of formula (VI), characterized in that:
A represents hydrogen, $R'_1$ and $R'_2$ represent a methyl group and $R_1$ represent an isopropyl group.

This novel compound consists of the following:
(E)-3,5-dimethoxy-4'-isopropyloxy-stilbene.

A particularly preferred aspect of the invention consists of the synthesis of (E)-trimethylresveratrol, (E)-tribenzylresveratrol and (E)-tetramethylpiceatannol from the compounds of formula (VII) as described above.

Preparation of the Polyhydroxystilbenes (Resveratrol and Piceatannol) from the (E)-Stilbene Derivatives of Formula (VI)

The (E)-stilbene derivatives of formula (VI) can be deprotected by processes known in the literature. This deprotection can be carried out by application or adaptation of the methods described, for example, in WO 2003/086414, WO 2001/060774, EP 1 466 884 or Tetrahedron, 59 (18), (2003), 3315-3321.

Under preferred processing conditions, use is made of 3 to 10 molar equivalents of boron tribromide at a temperature of between −30° C. and ambient temperature.

The (E)-hydroxystilbene derivatives of formula (VIII), for example in the form of resveratrol (B represents H), are thus obtained according to the scheme indicated below:

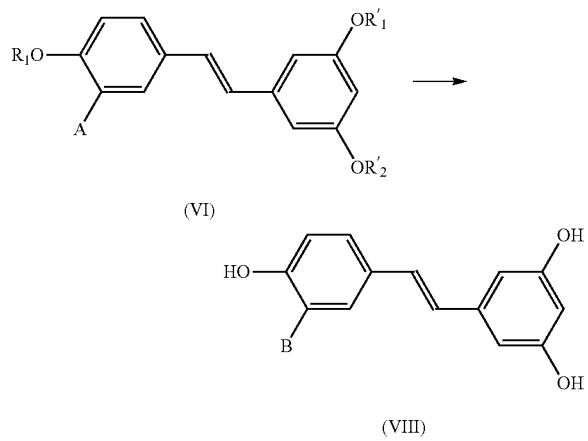

According to this method, it is possible, according to the process of the invention, to obtain resveratrol and piceatannol from the compounds of formula (IV) and more particularly from the compounds of formula (VII), defined above.

The present invention is also targeted at a process for the synthesis of a compound of formula (VII) as described above employing at least one compound chosen from those of formulae (I), (II), (III) and (IV), defined in the present patent application.

The present invention also covers any use of a compound of formula (I), (II), (III), (IV) or (VII) as defined above as intermediate in the synthesis of an (E)-stilbene derivative of formula (VI), in particular (E)-trimethylresveratrol, (E)-tribenzylresveratrol or (E)-tetramethylpiceatannol, or as intermediate in the synthesis of an (E)-polyhydroxystilbene compound, such as resveratrol or piceatannol.

The purpose of the following examples is to complete the present description without introducing a limitation to the invention.

EXAMPLE 1

Synthesis of methyl 3-(3,5-dimethoxyphenyl)-2-(4-methoxyphenyl)-3-oxopropionate 24.1 g of 60% sodium hydride in mineral oil (0.601 mol), which are washed with 2 times 60 ml of cyclohexane and 60 ml of THF, are introduced into a 1000 ml three-necked round-bottomed flask. A solution of 48.2 g of methyl 3,5-dimethoxybenzoate (0.243 mol) in 100 ml of THF is then introduced at ambient temperature. The mixture is brought to reflux and a solution of 43.8 g of methyl p-methoxyphenylacetate (0.243 mol) dissolved in 60 ml of THF is added over 10 h. The mixture is maintained at reflux for 5 h. It is cooled to a temperature of 0-5° C. and a solution of acetic acid (38.0 g, i.e. 0.633 mol) in 100 ml of THF is added over ½ hour at this temperature. Then, at ambient temperature, 150 ml of water are then added and the THF is distilled off. The medium is extracted with 500 ml of methyl tert-butyl ether (MTBE) and the organic phase is washed with 100 ml of a saturated aqueous sodium bicarbonate solution, washed with 50 ml of water and concentrated on a rotary evaporator to recover 74.4 g of crude β-ketoester in the form of a yellow oil, i.e. a crude yield of 89%.

200 ml of methanol are added to 60 g of this crude β-ketoester and this mixture is maintained at ambient temperature with stirring for 1 h. Subsequently, the precipitate obtained is filtered off and the operation is repeated with 150 ml of methanol. 24.7 g of white solid are recovered.

5 g of this precipitate are taken up in 50 ml of MTBE brought to reflux, the temperature is brought back to ambient temperature and an insoluble material (0.5 g) is filtered off. The filtrate is concentrated to dryness and the precipitate obtained is reslurried in 20 ml of methanol brought to reflux. After returning to ambient temperature, the precipitate which has formed is filtered off and washed on the filter with 5 ml of methanol. 3.6 g of a white solid are thus recovered, which solid exhibits a melting point of 76° C.

NMR (CDCl$_3$) 200 MHz

Proton: δ 3.75 s (3H); δ 3.8 s (9H); δ 5.5 s (1H); δ 6.6 t (1H); δ 6.9 d (2H); δ 7.1 d (2H); δ 7.35 d (2H);

C13 (Dept 135): δ 52.5 (COOCH$_3$); δ 55.07 and 55.37 (OCH$_3$); δ 59.49 (CH); δ 105.65 (arom. CH); δ 106.60; 114.20; 130.45 (arom CH).

EXAMPLE 2

Synthesis of methyl 3-(3,5-dibenzyloxyphenyl)-2-(4-benzyloxyphenyl)-3-oxopropionate 18.9 g of 60% sodium hydride in mineral oil (0.47 mol), which was washed with 2 times 50 ml of cyclohexane and then with 100 ml of THF, are introduced into a 1000 ml round-bottomed flask and then 65.7 g of methyl 3,5-dibenzyloxybenzoate (0.189 mol) in 100 ml of THF are introduced. The medium is brought to reflux and a solution of 48.3 g of methyl 4-benzyloxyphenylacetate (0.189 mol) in 120 ml of THF is added over 10 h. The mixture is maintained at reflux for 4 h and then cooled to 0-5° C. and a solution of 29.4 g of acetic acid (0.49 mol) in 240 ml of THF is added at this temperature. 360 ml of water are then added and the THF is distilled off at atmospheric pressure. 360 ml of MTBE are added, separation by settling is carried out and the organic phase is recovered and washed with 100 ml of a saturated aqueous sodium bicarbonate solution. The organic phase is concentrated on an rotary evaporator to result in 106.5 g of β-ketoester in the form of a viscous yellow oil, i.e. a crude yield of 98%.

1 g of this product, eluted on a column of silica (ethyl acetate/heptane 20/80), results in the recovery of 0.5 g of methyl 3-(3,5-dibenzyloxyphenyl)-2-(4-benzyloxyphenyl)-3-oxopropionate in the form of a viscous light yellow oil.

NMR (CDCl$_3$) 200 MHz

Proton: δ 3.75 s (3H); δ 5.05 s (6H); δ 5.48 s (1H); δ 6.78 t (1H); δ 6.95 d (2H); δ 7.15 d (2H); δ 7.28 d (2H).

C13: δ 52.8 (COOCH$_3$); δ 59.6 (CH); 70.1 and 70.4 (CH$_2$OPh); δ 107-160 (arom. CH); δ 169.6 (C=O).

EXAMPLE 3

Synthesis of methyl 3-(3,5-dimethoxyphenyl)-2-(3,4-dimethoxyphenyl)-3-oxopropionate 23.8 g of 60% NaH in mineral oil (0.59 mol) are introduced into a 1 l round-bottomed flask and are washed in the round-bottomed flask with 2 times 60 ml of cyclohexane, and then 46.7 g of methyl 3,5-methoxybenzoate (0.238 mol) dissolved in 200 ml of THF are added. The mixture is brought to reflux and 50 g of methyl 3,4-dimethoxyphenylacetate (0.238 mol) dissolved in 120 ml of THF are added over 10 h. The mixture is maintained at reflux for 2 h and cooled to 0-5° C. and 37.1 g (0.61 mol) of acetic acid diluted in 120 ml of THF are added dropwise at this temperature. 300 ml of water are then added and the THF is distilled off. The mixture is brought back to ambient temperature and extracted with 400 ml of MTBE, the organic phase is then washed with 100 ml of water and the medium is concentrated to recover 92.9 g of crude methyl 3-(3,5-dimethoxyphenyl)-2-(3,4-dimethoxyphenyl)-3-oxopropionate in the form of a viscous yellow oil.

NMR ($CDCl_3$) 200 MHz

Proton: δ 3.75 s (3H); δ 3.80 s (6H); δ 3.95 s (3H); δ 3.98 s (3H); δ 5.5 (1H); δ 6.5-7.3 m (6H)

C13: δ 52.5 ($COOCH_3$); δ 56.46 and 56.53 ($OCH_3$); δ 59.88 (CH); δ 99.67; 106.24; 111.50; 112.02; 121.02; 125.98; 146.48; 148.72; 149.29; 159.27 (arom. CH); δ 167.89 (C=O); δ 198.97 ($COOCH_3$).

EXAMPLE 4

Synthesis of 1-(3,5-dimethoxyphenyl)-2-(4-methoxyphenyl)ethanone 26.7 g of boric acid (0.43 mol) and 74.4 g of crude methyl 3-(3,5-dimethoxyphenyl)-2-(4-methoxyphenyl)-3-oxopropionate (0.216 mol) prepared according to Example 1 are introduced into a round-bottomed flask equipped with a distillation head. Heating is carried out, the temperature being brought gradually to 100° C. for 1 h, 120° C. for 1 h, 140° C. for 1 h and then 160° C. for 4 h while distilling off light products. The mixture is cooled to 80° C., 250 ml of water and then 200 ml of toluene are added, the mixture is kept stirred at 60° C. for 1 h, separation by settling is then carried out and the toluene phase is recovered, washed with 100 ml of a saturated aqueous sodium bicarbonate solution and concentrated on a rotary evaporator. The crude oily product obtained is taken up in 200 ml of MTBE to precipitate the product, which is filtered off and dried. Thus, after drying, 33.6 g of 1-(3,5-dimethoxyphenyl)-2-(4-methoxyphenyl)ethanone are obtained in the form of a cream-white solid, i.e. a yield of 54.4% with respect to the crude starting β-ketoester. M.p.: 93-4° C.

NMR ($CDCl_3$) 200 MHz

Proton: δ 3.5 s (3H); δ 3.6 ppm s (6H); δ 4.2 s (2H); δ 6.62 t (1H); δ 6.85 d (2H); δ 7.15 d (2H); δ 7.18 d (2H)

C13 (Dept 135): δ 44.6 ($CH_2$); δ 55.1 and 55.4 ($OCH_3$); δ 105.2; 106.3; 114; 130.2 (arom. CH).

EXAMPLE 5

Synthesis of 1-(3,5-dibenzyloxyphenyl)-2-(4-benzyloxyphenyl)ethanone 34.8 g of crude methyl 3-(3,5-dibenzyloxy-phenyl)-2-(4-benzyloxyphenyl)-3-oxopropionate prepared according to Example 2 (0.0608 mol) and 7.51 g of boric acid (0.121 mol) are introduced into a 250 ml round-bottomed flask. The medium is brought to 100° C. for 1 h, 120° C. for 1 h, 140° C. for 1 h and then 150-55° C. for 5 h while distilling off light products. The mixture is cooled to 60° C. and an aqueous solution of 8.5 g of sodium hydroxide pellets dissolved in 175 ml of water is added. The mixture is then brought to reflux for 3 h and brought back to 60° C., 250 ml of toluene are added, separation by settling is carried out, the organic phase is recovered and washed with 75 ml of water and then the toluene phase is concentrated on a rotary evaporator. 19.4 g of crude 1-(3,5-dibenzyloxyphenyl)-2-(4-benzyloxyphenyl) ethanone are recovered.

15 g of this crude product are brought to reflux in 140 ml of methanol and the mixture is cooled and maintained at 20-25° C. for 1 h. The precipitate obtained is filtered off, reslurried in 75 ml of methanol, filtered off and dried at 40° C. to result in 7 g of 1-(3,5-dibenzyloxyphenyl)-2-(4-benzyloxyphenyl) ethanone in the form of white solid, the melting point of which is 87° C.

NMR ($CDCl_3$) 200 MHz

Proton: δ 4.15 s (1H); δ 5.05 s (2H); δ 5.1 s (4H); δ 6.8 t (1H); δ 6.95 d (2H); δ 7.2 d (2H); δ 7.75 d (2H); δ 7.45 broad peak (15H)

C13: δ 44.5 ($CH_2$); δ 69.9 (O—$CH_2$-Ph); δ 70.2 (O—$CH_2$-Ph); δ 106.9-159.9 (arom. CH); δ 197.3 (C=O).

EXAMPLE 6

Synthesis of 1-(3,5-dimethoxyphenyl)-2-(3,4-dimethoxyphenyl)ethanone 90.9 g of crude methyl 3-(3,5-dimethoxyphenyl)-2-(3,4-dimethoxyphenyl)-3-oxopropionate prepared according to Example 3 and 30 g of boric acid are introduced into a 250 ml three-necked round-bottomed flask. The mixture is heated with stirring at 100° C. for 1 h, 120° C. for 1 140° C. for 1 h and then 160° C. for 4 h while distilling off light products. The mixture is cooled to approximately 60° C., 226 g of a 15% sodium hydroxide solution are added dropwise and the mixture is maintained at reflux for 2 h with stirring. The reaction medium is extracted at ambient temperature with 350 ml of toluene, which is washed with 100 ml of water. The organic phase is concentrated to recover 51.70 g of 1-(3,5-dimethoxyphenyl)-2-(3,4-dimethoxyphenyl)ethanone in the form of an oil with a dark brown colour.

1 g of crude ketone is purified from 25 ml of heptane, the insoluble heavy oil being removed and the precipitate which appears in the heptane solution after standing overnight being filtered off. 0.17 g of purified ketone is obtained, of M.p. 66° C.

NMR ($CDCl_3$) 200 MHz

Proton: δ 3.8 s (6H); δ 3.85 s (6H); δ 4.2 s (2H); δ 6.6-7.7 multiplet (6H).

C13: δ 45.25 ($CH_2$); δ 55.59; 55.91 ($OCH_3$); δ 105.35; 106.64; 111.56; 112.57; 121.62; 127.04; 138.56; 148.08; 149.12; 161.03 (arom. CH); δ 197.56 (C=O).

EXAMPLE 7

Synthesis of 1-(3,5-dimethoxyphenyl)-2-(4-methoxyphenyl)ethanol 160 ml of methanol, 32.6 g of recrystallized 1-(3,5-dimethoxyphenyl)-2-(4-methoxyphenyl)ethanone prepared according to Example 4 (114 mmol) and 3.25 g of 5% Pd/C of JM type 87 L are introduced into a hydrogenation reactor and hydrogen is introduced under a pressure of 5 to 6 bar at ambient temperature for 10 h. The catalyst is filtered off at 40° C. and the temperature is brought back to ambient temperature in order to recover 29 g of 1-(3,5-dimethoxyphenyl)-2-(4-methoxyphenyl)ethanol, i.e. a yield of 88.4% with respect to the starting ketone, which exhibits a melting point of 101-102° C.

NMR (CDCl$_3$) 200 MHz

Proton: δ 2.9 m (2H); δ 3.8 s (9H); δ q (1H); δ between 6.3 and 7.2 m (7H);

C13 (Dept 135): δ 44.9 (CH$_2$) δ 55.2 (OCH$_3$); δ 75.2 (CHOH); δ 99.9; 103.7; 113.8; 130.3 (arom. CH).

EXAMPLE 8

Synthesis of
1-(3,5-dimethoxyphenyl)-2-(4-methoxyphenyl)ethanol 5 g of precipitated 1-(3,5-dimethoxyphenyl)-2-(4-methoxyphenyl)ethanone (1.74 mmol) prepared according to Example 4 are introduced into 75 ml of methanol and 62.5 ml of THF in a 250 ml three-necked round-bottomed flask. 0.78 g of sodium borohydride (1.1 eq.) is added at ambient temperature over approximately 1 h. The reaction medium is kept stirred for 1 h and concentrated and the residue is taken up in 50 ml of a water/methanol (50/50 by volume) mixture. The precipitate obtained is filtered off and washed on the filter with 25 ml of water/methanol (50/50 by volume). 5 g of a white precipitate are recovered, which precipitate, by NMR, corresponds to the expected 1-(3,5-dimethoxyphenyl)-2-(4-methoxyphenyl)ethanol, i.e. a virtually quantitative yield.

EXAMPLE 9

Synthesis of 1-(3,5-dibenzyloxyphenyl)-2-(4-benzyloxyphenyl)ethanol 2 g (3.9 mmol) of recrystallized 1-(3,5-dibenzyloxyphenyl)-2-(4-benzyloxyphenyl)ethanone prepared according to Example 5 are introduced into a 100 ml round-bottomed flask and are dissolved in 30 ml of methanol and 25 ml of THF. Approximately 0.147 g of sodium borohydride is added in small fractions at ambient temperature over 1 hour. The medium is kept stirred for 1 h and concentrated, 30 ml of water are added and the medium is extracted with 60 ml of MTBE. The MTBE phase is concentrated to produce 2 g of a light yellow oil which crystallizes over time. 5 ml of methanol are added to this product, the mixture is kept stirred for 1 h and then the white precipitate obtained is filtered off. After drying at vacuum at 35° C., 1.3 g of 1-(3,5-dibenzyloxyphenyl)-2-(4-benzyloxyphenyl)ethanol are recovered in the form of a white solid with a melting point of 80-81° C., i.e. a yield of 65% with respect to the starting ketone.

NMR (CDCl$_3$) 200 MHz

Proton: δ 2 d (1H); δ 2.95 multiplet (2H); δ 4.8 multiplet (1H); δ 5.05 s (4H); δ 5.1 s (2H); δ 6.05 t (1H); δ 6.15 d (2H); δ 6.95 d (2H); δ 7.15 d (2H); δ 7.2-7.6 broad peak (15H).

C13: δ 44.88 (CH$_2$); δ 69.92 (O—CH$_2$); δ 75.2 (CHOH); δ 101.17; 104.98; 114.78; 127.31; 127.80; 128.44; 130.11; 130.40; 136.97; 146.36; 157.54; 159.86 (arom. CH).

EXAMPLE 10

Synthesis of 1-(3,5-dimethoxyphenyl)-2-(3,4-dimethoxyphenyl)ethanol 0.16 g (0.5 mmol) of 1-(3,5-dimethoxyphenyl)-2-(3,4-dimethoxyphenyl)ethanone synthesized and purified from heptane according to Example 6 is dissolved in 5 ml of methanol and 0.02 g of sodium borohydride is added at ambient temperature with stirring. The medium is kept stirred for 1 h and concentrated to dryness, 5 ml of water are added and the reaction medium is extracted with 10 ml of MTBE. The organic phase is washed with 5 ml of water and concentrated to result in 0.16 g of 1-(3,5-dimethoxyphenyl)-2-(3,4-dimethoxyphenyl)ethanol in the form of a colourless oil, i.e. a quantitative yield.

NMR (CDCl$_3$) 200 MHz

Proton: δ 2.95 multiplet (2H); δ 3.75 s (6H); δ 3.85 s (3H); δ 3.97 s (3H); δ 4.8 multiplet (1H); δ 6.35-7.28 broad unresolved peak (6H).

C13: δ 44.51 (CH$_2$); δ 54.34; 54.78; 54.88 (OCH$_3$); δ 74.29 (CH—OH); δ 98.51; 102.80; 110.22; 111.69; 120.49; 129.35; 145.42; 146.81; 147.83; 159.81 (arom. CH).

EXAMPLE 11

Synthesis of (E)-trimethylresveratrol 2 g of 1-(3,5-dimethoxyphenyl)-2-(4-methoxyphenyl) ethanol prepared according to Example 7 or Example 8 (6.9 mmol) and 0.019 g of p-toluenesulphonic acid (PTSA) monohydrate (6 mol %) are introduced into 200 ml of toluene in a 250 ml three-necked round-bottomed flask. The mixture is brought to reflux for 2 h 30 while removing the water by azeotropic distillation. The mixture is brought back to ambient temperature, 30 ml of a saturated sodium bicarbonate solution are added, washing is carried out with 30 ml of water and the toluene phase is concentrated to produce 1.95 g of a yellow oil. This oil is taken up in 3.8 ml of methanol and the mixture is brought to reflux and allowed to return to ambient temperature. The precipitate obtained is filtered off and washed on the filter with 1 ml of methanol. 1.31 g of light brown precipitate are recovered, which precipitate has a melting point of 55-56° C. and corresponds, by NMR, to (E)-trimethylresveratrol, i.e. a yield of 70%.

NMR (CDCl$_3$) 200 MHz

Proton: δ 3.83 s (9H); δ 6.40 t (1H); δ 6.68 d (2H); δ 6.9 d (1H); δ 6.92 d (2H); δ 7.10 d (1H); δ 7.48 d (2H)

C13: δ 55.32; 55.37 (OCH$_3$); δ 99.73; 104.49; 114.27; (arom. CH); 126.68; 128.84 (ethylen. CH); δ 127.97; 130.04; 139.84; 159.54; 161.13 (arom. CH).

EXAMPLE 12

Synthesis of (E)-tribenzylresveratrol 2 g of 1-(3,5-dibenzyloxyphenyl)-2-(4-benzyloxyphenyl) ethanol (3.9 mmol) prepared according to Example 9 and 0.04 g of PTSA monohydrate in 200 ml of toluene (6 mol %) are introduced into a 250 ml round-bottomed flask. The mixture is brought to reflux for 4 h while distilling off the water by azeotropic distillation. The mixture is cooled to ambient temperature, washing is carried out with 20 ml of saturated sodium bicarbonate solution and then with 10 ml of water, and the toluene phase is concentrated to produce 1.95 g of a cream white solid. This solid is taken up in 8 ml of MTBE and the mixture is kept stirred at ambient temperature for 2 h. The precipitate is filtered off and washed on the filter with 2 ml of MTBE. 0.99 g of brown oil is obtained, which oil crystallizes over time. The product is taken up at ambient temperature in 4 ml of MTBE. The product obtained is filtered off and washed on the filter with a small amount of MTBE to result in 0.42 g of a white, slightly cream, precipitate of 3,5,4'-tribenzylresveratrol with a melting point of 117-118° C., the NMR spectrum of which corresponds to that of (E)-tribenzylresveratrol.

NMR (CDCl$_3$) 200 MHz

Proton: δ 5.12 (6H); δ 6.63 t (1H); δ 6.83 d (2H); δ 6.95 d (1H); δ 7.02 d (1H); δ 7.1 d (1H); δ 7.3-7.6 broad unresolved peak (16H)

C13: δ 70.16; 70.24 (O—$\underline{C}$H$_2$); δ 101.40; 105.78; 115.24 (arom. $\underline{C}$H); δ 126.77 (eth$\underline{y}$len. $\underline{C}$H); δ 127.63; 128.00; 128.96 (arom. $\underline{C}$H); δ 130.29 (eth$\underline{y}$len. $\underline{C}$H); δ 137.03; 139.90; 158.76; 160.31 (arom. $\underline{C}$H).

EXAMPLE 13

Synthesis of N-[1-(3,5-dimethoxyphenyl)-2-(4-methoxyphenyl)ethylidene]-N'-tosylhydrazine 105.7 g (0.37 mol) of precipitated 1-(3,5-dimethoxyphenyl)-2-(4-methoxyphenyl)ethanone prepared according to Example 4 and 75.6 g (0.407 mol) of p-toluenesulphonylhydrazide are introduced into 950 ml of ethanol in a 2 l three-necked round-bottomed flask. The mixture is brought to reflux for 8 h and cooled to ambient temperature and then the precipitate obtained is filtered off and washed on the filter with a small amount of ethanol. 133.6 g of p-tosylhydrazone (80% yield) are obtained in the form of a slightly cream precipitate. The product is reslurried in 400 ml and then 860 ml of MTBE to result in 123.6 g of a white precipitate of N-[1-(3,5-dimethoxyphenyl)-2-(4-methoxyphenyl)ethylidene]-N'-tosylhydrazine, i.e. a yield of 74% with respect to the starting ketone, which exhibits a melting point of 120-121° C.

NMR (CDCl$_3$) 100 MHz

Proton: δ 2.4 s (3H); δ 3.8 s (9H); δ 2.4 s (3H); δ 3.9 s (2H); δ 2.4 s (3H); δ 6.4-7.8 m (11H)

C13: δ 21.4 (CH$_3$); δ 32.5 (CH$_2$); δ 55.04 and 55.23 (OCH$_3$); δ 143.9 (C=N); δ 100.3 and 161.4 (CH).

EXAMPLE 14

Synthesis of N-[1-(3,5-dibenzyloxyphenyl)-2-(4-benzyloxyphenyl)ethylidene]-N'-tosylhydrazine 5 g of 1-(3,5-dibenzyloxyphenyl)-2-(4-benzyloxyphenyl)ethanone prepared according to Example 5 (9.7 mmol), 2.35 g of p-toluenesulphonylhydrazide (12.6 mmol) in 25 ml of ethanol and 20 drops of 35% hydrochloric acid are introduced into 100 ml three-necked round-bottomed flask. The reaction medium is brought to reflux for 3 h and concentrated, the residue is taken up in 50 ml of MTBE at ambient temperature for 1 h with stirring and then the precipitate is filtered off and washed on the filter with a small amount of MTBE. 5.1 g of N-[1-(3,5-dibenzyloxyphenyl)-2-(4-benzyloxyphenyl)ethylidene]-N'-tosylhydrazine are obtained in the form of a white precipitate, i.e. a yield of 77% with respect to the starting ketone, which exhibits a melting point of 147° C.

NMR (CDCl$_3$) 200 MHz

Proton: δ 2.4 s (3H); δ 3.85 s (2H); δ 2.4 s (3H); δ 5.0 s (4H); δ 5.05 s (2H); δ 2.4 s (3H); δ 6.5-7.7 m (26H)

C13: δ 21.4 (CH$_3$); δ 32.5 (CH$_2$); δ 55.04 and 69.9 (OCH$_2$Ph); δ 143.8 (C=N); δ 100.3-159.8 (arom. CH).

EXAMPLE 15

Synthesis of N-[1-(3,5-dimethoxyphenyl)-2-(3,4-dimethoxyphenyl)ethylidene]-N'-tosylhydrazine 5 g (15.8 mmol) of crude 1-(3,5-dimethoxyphenyl)-2-(3,4-dimethoxyphenyl)ethanone prepared according to Example 6 and 3.24 g of p-toluenesulphonylhydrazide (17.4 mmol) are introduced into 33 ml of absolute ethanol in a 100 ml three-necked round-bottomed flask. The mixture is brought to reflux for 3 h, the temperature is brought back to ambient temperature and the mixture is left stirring for 2 h. The precipitate obtained is filtered off and then washed on the filter with 5 ml of ethanol. 5.25 g of precipitate are obtained, which precipitate is taken up in 50 ml of MTBE, brought to reflux for 2 h, filtered off after returning to ambient temperature and then washed on the filter with 10 ml of MTBE. 5 g of N-[1-(3,5-dimethoxyphenyl)-2-(3,4-dimethoxyphenyl)ethylidene]-N'-tosylhydrazine are recovered in the form of a white, slightly brown, solid, i.e. a yield of 65.4% with respect to the crude starting ketone, which exhibits a melting point of 132-133° C.

NMR (CDCl$_3$) 200 MHz

Proton: δ 2.5 s (3H); δ 3.6 s (3H); δ 3.75 s (6H); δ 3.8 s (3H); δ 3.85 s (2H); δ 6.4-7.8 m (10H)

C13: δ 21.95 (CH$_3$); δ 33.67 (CH$_2$); δ 55.80; 56.31; 56.41 (O$\underline{C}$H$_3$); δ 102.04; 105.21; 110.97; 112.08; 120.12; 126.16; 128.33; 135.63; 139.62; 129.95 (arom. $\underline{C}$H); δ 144.43 ($\underline{C}$=N); δ 148.74; 150.06; 154.03; 161.16 (arom. $\underline{C}$H).

EXAMPLE 16

Synthesis of (E)-trimethylresveratrol 50 g of N-[1-(3,5-dimethoxyphenyl)-2-(4-methoxyphenyl)ethylidene]-N'-tosylhydrazine prepared according to Example 13 (0.110 mol) and 27.16 g of potassium tert-butoxide (0.242 mol) in 1 l of toluene comprising 2.5 g of Triton X100® are introduced into a 2 l three-necked round-bottomed flask. The mixture is brought to reflux for 3 h, cooling is carried out to ambient temperature, 1 l of water is added, separation by settling is carried out and the organic phase is recovered. The aqueous phase is re-extracted with 0.4 liter of toluene. The combined organic phases are concentrated on a rotary evaporator to result in 29.6 g of crude product in the form of a yellow solid. This product is taken up in 90 ml of ethanol at ambient temperature overnight with stirring to result in 17.4 g of 3,5,4'-trimethylresveratrol in the form of a slightly orangey solid. The product is recrystallized on 34 ml of methanol and filtered at 0-5° C. to result in 16.6 g of (E)-trimethylresveratrol in the form of a white solid, i.e. a yield of 58% with respect to the starting hydrazone, which exhibits a melting point at 56-57° C.

NMR (CDCl$_3$) 200 MHz

Proton: δ 3.83 s (9H); δ 6.40 t (1H); δ 6.68 d (2H); δ 6.9 d (1H); δ 6.92 d (2H); δ 7.10 d (1H); δ 7.48 d (2H)

C13: δ 55.32; 55.37 (OCH$_3$); δ 99.73; 104.49; 114.27 (arom. $\underline{C}$H); 126.68; 128.84 (ethylen. $\underline{C}$H); δ 127.97; 130.04; 139.84; 159.54; 161.13 (arom. $\underline{C}$H).

EXAMPLE 17

Synthesis of (E)-trimethylresveratrol

The same reaction as in Example 16 is carried out on 2.5 g of N-[1-(3,5-dimethoxyphenyl)-2-(4-methoxyphenyl)ethylidene]-N'-tosylhydrazine in 12.5 ml of toluene in the presence of 1.36 g of potassium tert-butoxide and of 0.125 g of Triton X100® to result in 1.47 g of crude 3,5,4'-trimethylresveratrol, which is recrystallized from 5 ml of methanol to result in 0.91 g of (E)-trimethylresveratrol in the form of a white solid, i.e. a yield of 63.6% with respect to the starting hydrazone.

EXAMPLE 18

Synthesis of (E)-tribenzylresveratrol 28 g of N-[1-(3,5-dibenzyloxyphenyl)-2-(4-benzyloxyphenyl)ethylidene]-N'-tosylhydrazine (41 mmol) prepared as in Example 14 and 10.1 g of potassium tert-butoxide (100 mmol) in 560 ml of toluene comprising 1.4 g of Triton X100® are introduced into a 2 l three-necked round-bottomed flask. The mixture is brought to reflux for 3 h, the temperature is brought back to ambient temperature, 560 ml of water are added and the organic phase is separated by settling. The aqueous phase is re-extracted with 400 ml of toluene. The combined toluene phases are washed and concentrated to result in 21.8 g of crude product in the form of a yellow precipitate which is taken up in 70 ml of MTBE, filtered off and washed on the filter with MTBE to result in 11.9 g of (E)-tribenzylresveratrol which exhibits a melting point of 118° C., i.e. a yield of 58% with respect to the starting hydrazone.

NMR (CDCl$_3$) 200 MHz

Proton: δ 5.12 (6H); δ 6.63 t (1H); δ 6.83 d (2H); δ 6.95 d (1H); δ 7.02 d (1H); δ 7.1 d (1H); δ 7.3-7.6 broad unresolved peak (16H)

C13: δ 70.16 and 70.24 (O—CH$_2$); δ 101.40; 105.78; 115.24 (arom. CH); δ 126.77 (ethylen. CH); δ 127.63; 128.00; 128.96 (arom. CH); δ 130.29 (ethylen. CH); δ 137.03; 139.90; 158.76; 160.31 (arom. CH).

EXAMPLE 19

Synthesis of (E)-tribenzylresveratrol 1.46 g of N-[1-(3,5-dibenzyloxyphenyl)-2-(4-benzyloxyphenyl)ethylidene]-N'-tosylhydrazine (2.1 mmol) prepared as in Example 14 and 0.28 g of potassium hydroxide (85%) pellets in 30 ml of toluene comprising 0.07 g of Triton X100® are introduced into a 100 ml three-necked round-bottomed flask. The mixture is brought to reflux for 2 h. 30 ml of water are added at ambient temperature, separation by settling is carried out and the toluene phase is recovered and washed with 15 ml of water. The toluene phase is concentrated to result in 1 g of solid in the form of a yellow precipitate, which precipitate is taken up in 4 ml of MTBE to result, after filtration, in 0.8 g of (E)-tribenzylresveratrol, i.e. a yield of 76% with respect to the starting hydrazone.

EXAMPLE 20

Synthesis of (E)-tetramethylpiceatannol 2.6 g (5.0 mmol) of N-[1-(3,5-dimethoxyphenyl)-2-(3,4-dimethoxyphenyl)ethylidene]-N'-tosylhydrazine prepared according to Example 15, 1.24 g (11.4 mmol) of potassium tert-butoxide and 0.13 g of Triton X100® are introduced into 25 ml of toluene in a 100 ml three-necked round-bottomed flask. The mixture is brought to reflux for 3 h. The temperature is brought back to approximately 90° C., 15 ml of water are added dropwise, the medium is separated by settling at approximately 60° C., the organic phase is washed with 15 ml of water and the organic phase is concentrated on a rotary evaporator to recover 1.55 g of a slightly brown oil. This oil is taken up in 10 ml of methanol. The temperature is brought back to ambient temperature and the mixture is maintained at ambient temperature for 2 h. The precipitate is filtered off and washed on the filter with 3 ml of methanol. 1.03 g of (E)-tetramethylpiceatannol are recovered in the form of a white, slightly cream, precipitate, i.e. a yield of 68.6% with respect to the starting hydrazone, which exhibits a melting point of 68° C.

NMR (CDCl$_3$) 200 MHz

Proton: δ 3.8 s (6H); δ 3.88 s (3H); δ 3.92 s (3H); δ 6.40 t (1H); δ 6.68 d (2H); 6.85 d (1H); δ 6.95 d (1H); δ 6.98-7.12 m (3H).

C13 (Dept 135): δ 55.38 and 55.97 (OCH$_3$); δ 99.75; 104.40; 108.84; 120.08 (arom. CH); δ 126.81; 129.03 (ethylen. CH).

EXAMPLE 21

Synthesis of (E)-tetramethylpiceatannol 2 g (3.86 mmol) of N-[1-(3,5-dimethoxyphenyl)-2-(3,4-dimethoxyphenyl)ethylidene]-N'-tosylhydrazine prepared according to Example 15, 0.97 g of potassium tert-butoxide (2.1 eq.) and 0.10 g of Triton X100® are introduced into 20 ml of mesitylene in a 50 ml three-necked round-bottomed flask. The medium is brought to reflux for 2 h and then brought back to a temperature of 60° C., 10 ml of water are added, separating by settling is carried out and the organic phase is recovered and washed with 5 ml of water. The organic phase is concentrated up to 80° C. under 5 mmHg. 1.06 g of a yellow oil are recovered. This oil is brought to reflux in 6 ml of methanol, the temperature is brought back to ambient temperature, the mixture is kept stirred for 2 h and the precipitate is filtered off and washed on the filter with 2 ml of methanol. 0.55 g of (E)-tetramethylpiceatannol is recovered in the form of a white, slightly yellow, precipitate, i.e. a yield of 47.8% with respect to the starting hydrazone.

EXAMPLE 22

Synthesis of (E)-tetramethylpiceatannol 2 g (3.86 mmol) of N-[1-(3,5-dimethoxyphenyl)-2-(3,4-dimethoxyphenyl)ethylidene]-N'-tosylhydrazine prepared according to Example 15, 0.431 g of sodium methoxide and 0.10 g of Triton X100® are introduced into 20 ml of toluene in a 50 ml three-necked round-bottomed flask. The medium is brought to reflux for 5 h, and cooled to approximately 60° C., 10 ml of water are slowly added and separation by settling is carried out at this temperature. The toluene phase is washed with 5 ml of water and the organic phase is concentrated on a rotary evaporator to result in 1.18 g of an orangey oil. This oil is brought to reflux in 6 ml of methanol, the temperature is brought back to ambient temperature, the mixture is kept stirred for 2 h and the precipitate is filtered off and washed on the filter with 2 ml of methanol. 0.68 g of (E)-tetramethylpiceatannol is recovered in the form of a white, slightly yellow, precipitate, i.e. a yield of 59.1% with respect to the starting hydrazone.

EXAMPLE 23

Synthesis of (E)-tetramethylpiceatannol

The same reaction is carried out as in Example 22 but with 0.34 g of 60% NaH in oil (8.5 mmol) which has been washed beforehand in the round-bottomed flask with 2 times 5 ml of cyclohexane. The mixture is maintained by reflux for 3 h and the treatment is carried out as in Example 22 to produce 1.32 g of an orangey-yellow oil. After precipitating from 7 ml of methanol as in Example 22, 0.66 g of a white, slightly orangey, solid formed of (E)-tetramethylpiceatannol is recovered, i.e. a yield of 57.4% with respect to the starting hydrazone.

EXAMPLE 24

Synthesis of (E)-resveratrol 37.9 ml of boron tribromide (approximately 100 g, 400 mmol) are introduced into 100 ml of methylene chloride under a nitrogen atmosphere in a three-necked round-bottomed flask. The medium is cooled to approximately –20° C. and 10.8 g (approximately 40 mmol) of (E)-trimethylresveratrol dissolved in 20 ml of methylene chloride are introduced at this temperature over 1 h 30. The medium is allowed to return to ambient temperature with stirring and is left stirring at this temperature for 4 hours. The reaction medium is then slowly poured onto 800 g of an ice/water mixture. The medium is extracted with 325 ml and then 200 ml of MTBE and the organic phases are washed with 2 times 75 ml of a saturated sodium bicarbonate solution and then with 75 ml of water. The combined organic phases are concentrated on a rotary evaporator. The solid residue is taken up in 100 ml of methylene chloride, filtered off and dried to result in 8.1 g of crude resveratrol.

The precipitate is dissolved in ethanol at 60° C. and precipitated by addition of water to result in resveratrol with a melting point of 262-264° C. The proton and C13 NMR spectra correspond to the expected product.

EXAMPLE 25

Synthesis of methyl 3-(3,5-dimethoxyphenyl)-2-(4-isopropyloxyphenyl)-3-oxopropionate 14.4 g of 60% sodium hydride in mineral oil (0.36 mol) which are washed with 2 times 50 ml of toluene are introduced into a three-necked round-bottomed flask. 90 ml of toluene and 28.3 g of methyl 3,5-dimethoxybenzoate (0.144 mol) are then introduced. The mixture is brought to reflux and a solution of 30 g of methyl p-isopropyloxyphenylacetate (0.144 mol) dissolved in 95 ml of toluene is added over 10 h. The mixture is maintained at reflux for 2 h. It is cooled to a temperature of 0-5° C. and a solution of glacial acetic acid (22.5 g, i.e. 0.374 mol) in 25 ml of toluene is added slowly. Then, at ambient temperature, 135 ml of water are added slowly.

The organic phase is decanted and the aqueous phase is extracted with 25 ml of toluene. The combined toluene phases are concentrated to result in 58 g of crude methyl 3-(3,5-dimethoxyphenyl)-2-(4-isopropyloxyphenyl)-3-oxopropionate in the form of a viscous oil with a dark brown color.

NMR (CDCl$_3$) 200 MHz
Proton: δ 1.35 d (6H); δ 3.75 s (3H); δ 3.8 s (6H); δ 4.5 hept (1H); δ 5.5 s (1H); δ 6.6 t (1H); δ 6.85 d (2H); δ 7.10 d (2H); δ 7.30 d (2H);
C13 (Dept 135): δ 22 (CH$_3$—CH); δ 52.7 (COOCH$_3$); δ 55.5 (2 OCH$_3$); δ 59.7 (C$\overline{H}$—COOMe); δ 69.9 (CH$\overline{-}$CH$_3$); δ 105.8; $\overline{1}$06.8; 116.0; 1$\overline{3}$0.7 (arom. CH).

EXAMPLE 26

Synthesis of methyl 3-(3,5-dimethoxyphenyl)-2-(3,4-methylenedioxyphenyl-3-oxopropionate 19.7 g of 60% sodium hydride in mineral oil (0.49 mol) which are washed with 2 times 60 ml of toluene are introduced into a three-necked round-bottomed flask. 120 ml of toluene, 4 g of triton X100® (and 38.6 g of methyl 3,5-dimethoxybenzoate (0.197 mol) are then introduced. The mixture is brought to reflux and a solution of 38.2 g of methyle 3,4-methylenedioxyphenylacetate (0.197 mol) dissolved in 130 ml of toluene is added over 10 h. The mixture is maintained at reflux for 2 h. It is cooled to a temperature of 0-5° C. and a solution of glacial acetic acid (30.7 g, i.e. 0.51 mol) in 30 ml of toluene is added drop by drop. The mixture is maintained 1 h under agitation while returning to ambient temperature, then 180 ml of water are added slowly and the organic phase is recovered. The aqueous phase is re-extracted with 40 ml of toluene. The combined organic phases are concentrated to result in 76.5 g of crude methyl 3-(3,5-dimethoxyphenyl)-2-(3,4-methylenedioxyphenyl-3-oxopropionate in the form of a viscous oil with a dark color.

1 ml of methanol is added to 1 g of this crude product to result in a white precipitate which is filtered, washed on the filter with methanol and dried, which precipitate has a melting point of 51° C.

NMR (CDCl$_3$) 200 MHz
Proton: δ 3.75 s (3H); δ 3.8 s (6H); δ 5.5 s (1H); δ 5.95 m (2H); δ 6.6 t (1H); δ 6.8 to 7.3 arom. (5H);
C13 (Dept 135): δ 52.8 (COOCH$_3$); δ 55.6 (2 OCH$_3$); δ 59.9 (C$\overline{H}$—COOMe); δ 101.3 $\overline{(O}$—CH2—O); δ$\overline{\ }$105.9; 106.8; $\overline{1}$08.6; 109.8; 123.1 (arom. CH).$\overline{\ }$

EXAMPLE 27

Synthesis of 1-(3,5-dimethoxyphenyl)-2-(4-isopropyloxyphenyl)ethanone 9.65 g of boric acid (0.16 mol) and 58 g of crude methyl 3-(3,5-dimethoxyphenyl)-2-(4-isopropyloxyphenyl)-3-oxopropionate (0.16 mol) prepared according to Example 25 are introduced into a round-bottomed flask. The mixture is heated with stirring at 150-155° C. for 3 h and then cooled to approximately 80° C. 200 ml of toluene and then 150 ml of water are added. Separation by settling is carried out and the organic phase is recovered. The aqueous phase is re-extracted with 20 ml of toluene. The organic phases are concentrated to recover 48.8 g of crude 1-(3,5-dimethoxyphenyl)-2-(4-isopropyloxyphenyl)ethanone in the form of a viscous oil with a dark brown color.

NMR (CDCl$_3$) 200 MHz
Proton: δ 1.35 d (6H); δ 3.8 s (6H); δ 4.2 s (2H); δ 4.5 hept (1H); δ 6.6 t (1H); δ 6.85 d (2H); δ 7.15 d (2H); δ 7.20 d (2H);
C13 (Dept 135): δ 22.1 (CH$_3$—CH); δ 44.8 (CH$_2$); δ 55.5 (2 OCH$_3$); δ 69.9 (CH—C$\overline{H}_3$); δ 105.3; 106.5; $\overline{1}$16.1; 130.5 (aro$\overline{m}$. CH).

EXAMPLE 28

Synthesis of 1-(3,5-dimethoxyphenyl)-2-(3,4-methylenedioxyphenyl)ethanone 13 g of boric acid (0.21 mol) and 75 g of crude methyl 3-(3,5-dimethoxyphenyl)-2-(3,4-methylenedioxyphenyl-3-oxopropionate (0.21 mol) prepared according to Example 26 are introduced into a round-bottomed flask. The medium is brought to 140° C. to 1 h and then heated to 150-155° C. for 3 h. The mixture is cooled to 80° C., 360 ml of toluene and then 190 ml of water are added. Separation by settling is carried out and the aqueous phase is re-extracted with 70 ml of toluene. The organic phases are concentrated to recover 63.6 g of a brown solid which is taken up in 100 ml of ethanol. The precipitate is filtered off, washed on the filter with 25 ml of ethanol and dried to result in 44.7 g of crude 1-(3,5-dimethoxyphenyl)-2-(3,4-methylenedioxyphenyl)ethanone in the form of a cream solid, i.e. a yield of 71% with respect to the crude starting keto-ester.

2 g of this product is recrystallised with 20 ml of ethanol to result in a white precipitate having a melting point of 123° C.

NMR (CDCl$_3$) 200 MHz

Proton: δ 3.85 s (6H); δ 4.2 s (2H); δ 5.95 s (2H); δ 6.65 t (1H); δ 6.7-6.8 m (3H); δ 7.15 d (2H);

C13 (Dept 135): δ 45.3 (CH$_2$—CO); δ 55.6 (2 OCH$_3$); δ 101.0 (O—CH$_2$—O); δ 105.4; 106.5; 108.5; 109.9; 122.6 (arom. CH)

EXAMPLE 29

Synthesis of N-[1-(3,5-dimethoxyphenyl)-2-(4-isopropyloxyphenyl)ethylidene]-N'-tosylhydrazine 48.5 g (0.14 mol) of crude 1-(3,5-dimethoxyphenyl)-2-(4-isopropyloxyphenyl)ethanone prepared according to Example 27 and 31.8 g (0.17 mol) of p-toluenesulphonylhydrazide are introduced into 250 ml of ethanol in a three-necked round-bottomed flask. The mixture is brought to reflux for 6 h, cooled to ambient temperature and the mixture is left stirring for 5 h. Then the precipitate obtained is filtered off and washed on the filter with 25 ml of ethanol. The precipitate is taken up in 100 ml of MTBE at ambient temperature for 1 h with stirring and then the precipitate is filtered off and washed on the filter with 25 ml of MTBE and dried. 31.4 g of N-[1-(3,5-dimethoxyphenyl)-2-(4-isopropyloxyphenyl)ethylidene]-N'-tosylhydrazine are recovered in the form of a white solid which exhibits a melting point of 101° C., i.e. a yield of 42% with respect to the crude starting ketone.

NMR (CDCl$_3$) 200 MHz

Proton: δ 1.35 d (6H); δ 2.4 s (3H); δ 3.8 s (6H); δ 3.9 s (2H); δ 4.5 hept (1H); δ 6.4 t (1H); δ 6.7 d (2H); δ 6.83 d (2H); δ 6.85 d (2H); δ 7.25 d (2H); δ 7.68 d (2H);

C13 (Dept 135): δ 21.7 (CH$_3$); δ 22.0 (CH$_3$—CH); δ 32.7 (CH$_2$); δ 55.4 (2 OCH$_3$); δ 69.9 (CH—CH$_3$); δ 101.7; 104.8; 116.7; 128.0; 128.8; 129.5 (arom. CH).

EXAMPLE 30

Synthesis of N-[1-(3,5-dimethoxyphenyl)-2-(3,4-methylenedioxyphenyl)ethylidene]-N'-tosylhydrazine 42.7 g (0.142 mol) of 1-(3,5-dimethoxyphenyl)-2-(3,4-methylenedioxyphenyl)ethanone prepared according to Example 28 and 29 g (0.155 mol) of p-toluenesulphonylhydrazide are introduced into 270 ml of ethanol in a three-necked round-bottomed flask. The mixture is brought to reflux for 5 h, cooled to ambient temperature, left stirring for 3 h and then 2 h at 0-5° C. The precipitate obtained is filtered off and washed on the filter with 20 ml of ethanol cooled to 0-5° C. The precipitate is taken up in 100 ml of MTBE, filtered off and dried to recover 44.6 g of N-[1-(3,5-dimethoxyphenyl)-2-(3,4-methylenedioxyphenyl)ethylidene]-N'-tosylhydrazine in the form of a cream solid which exhibits a melting point of 143-144° C., i.e. a yield of 67% with respect to the starting ketone.

NMR (CDCl$_3$) 200 MHz

Proton: δ 2.4 s (3H); δ 3.75 s (6H); δ 3.85 s (2H); δ 5.95 s (2H); δ 6.35 d (1H); δ 6.45 t (1H); δ 6.6 d (1H); δ 6.8 d (2H); δ 7.25 d (2H); δ 7.25 s (1H); δ 7.7 d (2H);

C13 (Dept 135): δ 21.7 (CH$_3$); δ 33.1 (CH$_2$—CN—); δ 55.5 (2 OCH$_3$); δ 101.3 (O—CH$_2$—O); δ 101.7; 104.8; 108.2; 108.8; 120.6; 128.0; 129.5 (arom. CH)

EXAMPLE 31

Synthesis of (E)-3,5-dimethoxy-4'-isopropyloxy-stilbene 19 g of N-[1-(3,5-dimethoxyphenyl)-2-(3,4-methylenedioxyphenyl)ethylidene]-N'-tosylhydrazine (0.39 mol) prepared as in Example 29. 9.3 g of potassium ter-butoxide (0.83 mol) and 1.9 g of Triton X100® are introduced into a three-necked round-bottomed flask comprising 100 ml of toluene. The mixture is brought to reflux for 3 h, cooled to approximately 90° C. and 70 ml of water are introduced. Separation by settling is carried out and the aqueous phase is re-extracted with 50 ml of toluene. The toluene phases are washed with 50 ml of water and concentrated to result in 12.3 g of a viscous product with a yellow color, which is taken up in 10 ml of methanol and maintained for 3 h under agitation. The precipitate is filtered off, washed on the filter with methanol and dried. 6.5 g of (E)-3,5-dimethoxy-4'-isopropyloxy-stilbene is recovered in the form of a white solid, which exhibits a melting point of 61° C., i.e. a yield of 55.6% with respect to the starting hydrazone.

NMR (CDCl$_3$) 200 MHz

Proton: δ 1.35 d (6H); δ 3.85 s (6H); δ 4.6 hept (1H); δ 6.4 t (1H); δ 6.7 d (2H); δ 6.9 d (1H); δ 6.93 d (2H); δ 7.09 d (1H); δ 7.45 d (2H);

C13 (Dept 135): δ 22.5 (CH$_3$—CH); δ 55.7 (2 OCH$_3$); δ 70.3 (CH—CH$_3$); δ 100.0; 104.8; 116.4 (arom. CH); δ 126.9; 128.2 (CH═); δ 129.2 (arom. CH)

EXAMPLE 32

Synthesis of (E)-3,5-dimethoxy-3',4'-methylenedioxy-stilbene 39.4 g of N-[1-(3,5-dimethoxyphenyl)-2-(3,4-methylenedioxyphenyl)ethylidene]-N'-tosylhydrazine (0.084 mol) prepared as in Example 30, 19.9 g of potassium ter-butoxide (0.177 mol) and 3.9 g of Triton X100® are introduced into a three-necked round-bottomed flask comprising 190 ml of toluene. The mixture is brought to reflux for 4 h, cooled to approximately 80° C. and 130 ml of water are introduced. Separation by settling is carried out and the aqueous phase is re-extracted with 90 ml of toluene. The toluene phases are washed with 50 ml of water and concentrated to result in 27.8 g of a brown solid, which is taken up in 30 ml of methanol and maintained for 1 h under agitation. The precipitate is filtered off, washed on the filter with methanol and dried. 16.6 g of (E)-3,5-dimethoxy-3',4'-methylenedioxy-stilbene is recovered in the form of a brown solid, which exhibits a melting point of 96° C., i.e. a yield of 69% with respect to the starting hydrazone.

NMR (CDCl$_3$) 200 MHz

Proton: δ 3.8 s (6H); δ 6 s (2H); δ 6.4 t (1H); δ 6.65 t (2H); δ 6.8 d (1H); δ 6.9 d (1H); δ 6.95 d (1H); δ 7.05 d (1H); δ 7.25 s (1H);

C13 (Dept 135): δ 55.5 (2 OCH$_3$); δ 99.8 (arom. CH); δ 101.2 (O—CH$_2$—O); δ 104.4; 105.6; 108.5; 121.7; 127.0; 128.9 (arom. CH)

The invention claimed is:
1. A process for the synthesis of an (E)-stilbene derivative of formula (VI)

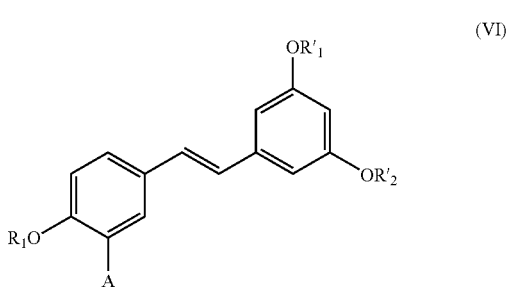

in which
A represents hydrogen or an OR$_2$ group, and
R$_1$, R$_2$, R'$_1$ and R'$_2$ represent, independently of one another, a linear or branched alkyl group comprising from 1 to 6 carbon atoms or an aralkyl group including from 7 to 16 carbon atoms which is optionally substituted by one or more alkoxy or halogen groups, or wherein R$_1$ and R$_2$ form a hydrocarbon chain of structure —(CH$_2$)$_n$— with n=1 to 3,
said process comprising reacting in a decarboxylation step a compound of formula (III)

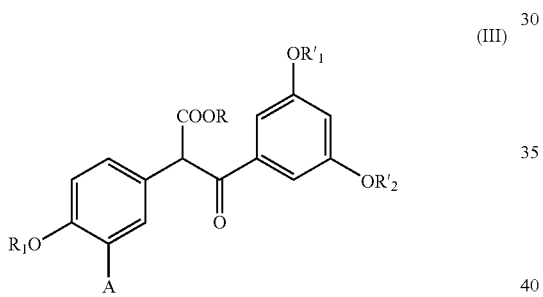

in which A, R$_1$, R$_2$, R'$_1$ and R'$_2$ are as defined above, R is a linear or branched alkyl group comprising from 1 to 6 carbon atoms to provide a compound of formula (IV)

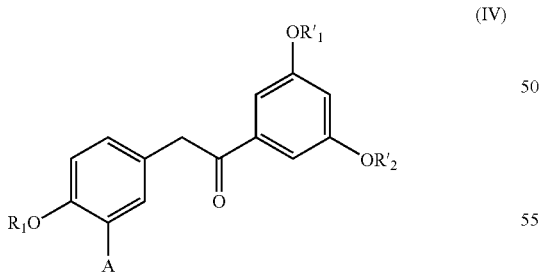

in which A, R$_1$, R$_2$, R'$_1$ and R'$_2$ are as defined above, and in a second reaction step:
a) reducing the compound of formula (IV) to form an alcohol and subsequently dehydrating the alcohol, or
b) reacting the compound of formula (IV) with an arylsulphonylhydrazide to form an arylsulphonylhydrazone and subsequently reacting the arylsulphonylhydrazone with a base,
to obtain the (E)-stilbene derivative of formula (VI).

2. The process of claim 1, wherein the compound of formula (IV) is reduced in a reduction reaction to form an alcohol of formula (V)

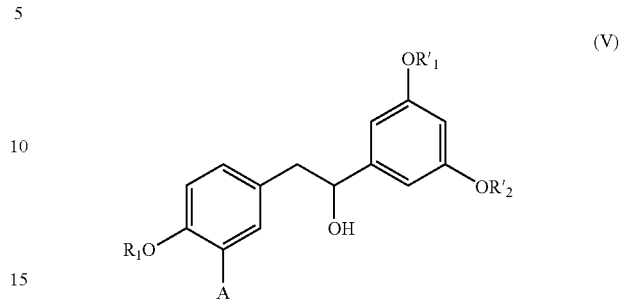

in which
A represents hydrogen or else an OR$_2$ group,
R$_1$, R$_2$, R'$_1$ and R'$_2$ represent, independently of one another, a linear or branched alkyl group comprising from 1 to 6 carbon atoms or an aralkyl group including from 7 to 16 carbon atoms which is optionally substituted by one or more alkoxy or halogen groups, or wherein R$_1$ and R$_2$ form a hydrocarbon chain of structure —(CH$_2$)$_n$— with n=1 to 3,
to form 1,2-diarylethanol derivatives of formula (V), and subsequently dehydrating the 1,2-diarylethanol derivatives of formula (V) to form the compounds of formula (VI)

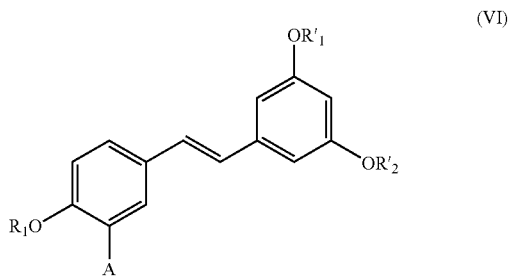

in which A, R$_1$, R$_2$, R'$_1$ and R'$_2$ are as defined above.

3. The process of claim 2, wherein the reduction reaction is carried out in the presence of a metal hydride.

4. The process of claim 2, wherein the reduction reaction is carried out by hydrogenation of the ketones of formula (IV)

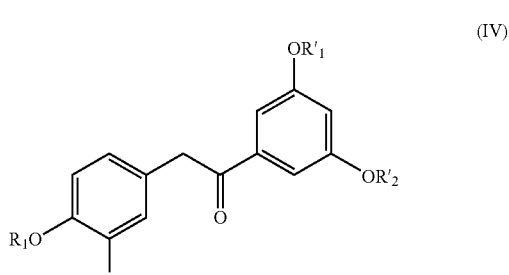

in which
A represents hydrogen or an OR$_2$ group,
R$_1$, R$_2$, R'$_1$ and R'$_2$ represent, independently of one another, a linear or branched alkyl group comprising from 1 to 6 carbon atoms, or wherein $R_1$ and $R_2$ form a hydrocarbon chain of structure —$(CH_2)_n$— with n=1 to 3.

5. The process of claim 2, wherein the dehydration of the compound of formula (V) is carried out in the presence of a catalytic amount of strong acid.

6. The process of claim 1, wherein the compound of formula (IV)

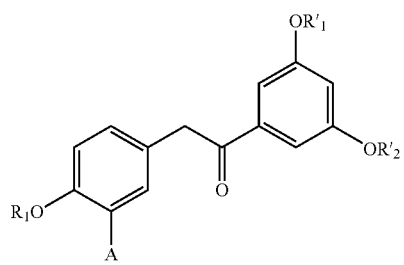
(IV)

in which

A represents hydrogen or an $OR_2$ group, and $R_1, R_2, R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups, or wherein $R_1$ and $R_2$ form a hydrocarbon chain of structure —$(CH_2)_n$— with n=1 to 3, is reacted with an arylsulphonylhydrazide compound to produce an intermediate arylsulphonylhydrazone compound of formula (VII)

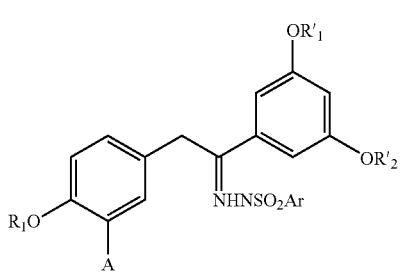
(VII)

in which

Ar represents a phenyl or o-, m- or p-tolyl group,

A represents hydrogen or else an $OR_2$ group, $R_1, R_2, R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups, or wherein $R_1$ and $R_2$ form a hydrocarbon chain of structure —$(CH_2)_n$— with n=1 to 3, and subsequently reacting the compound of formula (VII) with a strong base.

7. The process of claim 6, wherein the compound of formula (VII) is treated in the presence of a compound selected form the group consisting of an alkali metal alkoxide, an alkali metal hydride, an alkaline base, sodium carbonate and potassium carbonate to obtain the compound of formula (VI)

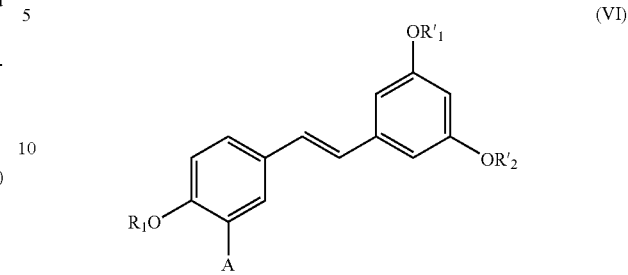
(VI)

in which

A represents hydrogen or an $OR_2$ group, $R_1, R_2, R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups, or wherein $R_1$ and $R_2$ form a hydrocarbon chain of structure —$(CH_2)_n$— with n=1 to 3.

8. The process of claim 6, wherein the reaction of the compound of formula (VII) with a strong base is carried out in the presence of a solvent having a boiling point of at least 90° C.

9. The process of claim 6, wherein the reaction of the compound of formula (VII) with a strong base is carried out in the presence of a nonhydroxylated solvent.

10. The process of claim 1, further comprising reacting in a condensation step ether/ester derivatives of formula (I) and ether/ester derivatives of formula (II)

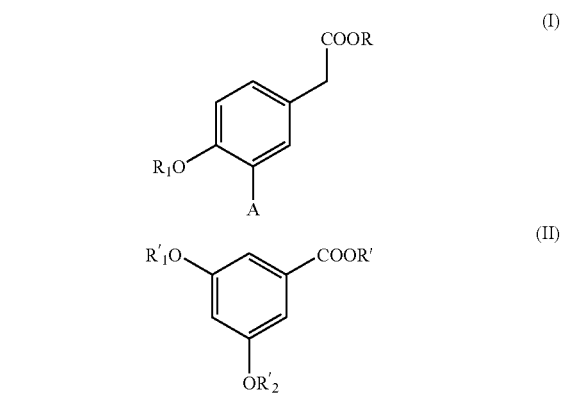

in which

A represents hydrogen or else an $OR_2$ group, $R_1, R_2, R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups, or wherein $R_1$ and $R_2$ form a hydrocarbon chain of structure —$(CH_2)_n$— with n=1 to 3, R and R' represent, independently of one another, a linear or branched alkyl group comprising from 1 to 6 carbon atoms, in the presence of a strong base to provide the compound of formula (III)

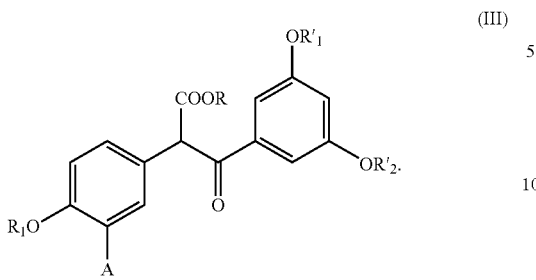

11. The process of claim 10, wherein the ether/esters of formulae (I) and (II) are obtained from hydroxyaromatic acids, hydroxyaromatic esters or etherified hydroxyaromatic acids.

12. The process of claim 11, wherein the hydroxyaromatic acids are selected from the group consisting of 4-hydroxyphenylacetic acid, resorcylic acid, and 3,4-dihydroxyphenylacetic acid.

13. The process of claim 1, wherein the (E)-stilbene derivative of formula (VI) is selected from the group consisting of (E)-trimethylresveratrol, (E)-tribenzylresveratrol, and (E)-tetramethylpiceatannol.

14. A process for the synthesis of an (E)-stilbene derivative of formula (VI)

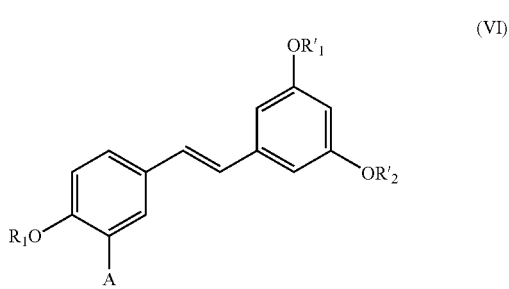

in which
A represents hydrogen or an $OR_2$ group, and
$R_1, R_2, R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups, or wherein $R_1$ and $R_2$ form a hydrocarbon chain of structure —$(CH_2)_n$— with n=1 to 3,
said process comprising reacting in a first reaction step a compound of formula (IV)

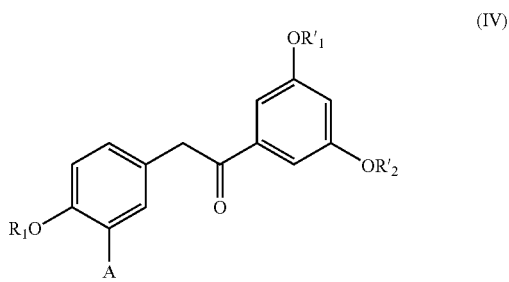

in which A, $R_1$, $R_2$, $R'_1$ and $R'_2$ are as defined above, with an arylsulphonylhydrazide to obtain an arylsulphonylhydrazone of formula (VII)

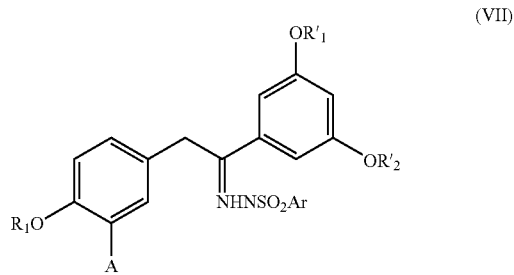

in which A, $R_1$, $R_2$, $R'_1$ and $R'_2$ are as defined above and Ar represents a phenyl or o-, m- or p-tolyl group, and
further reacting in a second reaction step the arylsulphonylhydrazone of formula (VII) with a base,
to obtain the (E)-stilbene derivative of formula (VI).

15. The process of claim 14, wherein the second reaction step is carried out in the presence of a strong base.

16. The process of claim 14, wherein the second reaction step is carried out in the presence of a base selected from the group consisting of an alkali metal alkoxide, an alkali metal hydride, an alkaline base, sodium carbonate and potassium carbonate to obtain the compound of formula (VI)

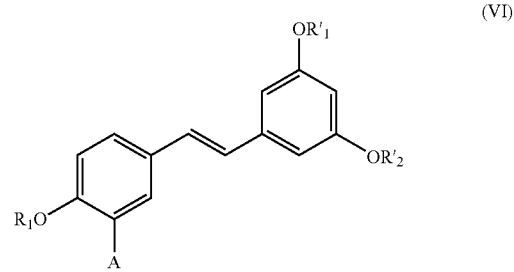

in which
A represents hydrogen or an $OR_2$ group, and
$R_1, R_2, R'_1$ and $R'_2$ represent, independently of one another, a linear or branched alkyl group comprising from 1 to 6 carbon atoms or an aralkyl group including from 7 to 16 carbon atoms which is optionally substituted by one or more alkoxy or halogen groups, or wherein $R_1$ and $R_2$ for a hydrocarbon chain of structure —$(CH_2)_n$— with n=1 to 3.

17. The process of claim 14, wherein the second reaction step is carried out in the presence of a solvent having a boiling point of at least 90° C.

18. The process of claim 14, wherein the second reaction step is carried out in the presence of a nonhydroxylated solvent.

19. Compound of formula (III)

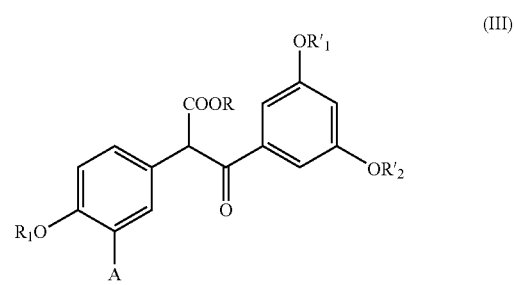

in which

R represents a methyl group, and

A represents hydrogen and the $R_1$, $R'_1$ and $R'_2$ groups represent methyl groups or benzyl groups, or A represents an —$OCH_3$ group and the $R_1$, $R'_1$ and $R'_2$ groups each represent a methyl group, or A represents hydrogen, $R'_1$ and $R'_2$ represent a methyl group and $R_1$ represents an isopropyl group, or A represents an —$OR_2$ group, $R'_1$ and $R'_2$ represent a methyl group and $R_1$ and $R_2$ form a hydrocarbon chain of structure —$(CH_2)_n$— with n=1.

20. Compound of formula (V)

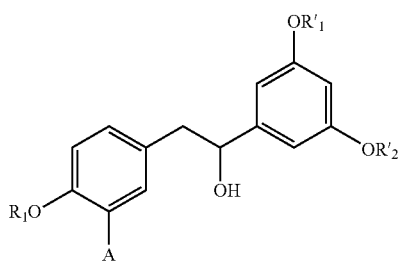

(V)

in which

A represents hydrogen and $R_1$, $R'_1$ and $R'_2$ each represent a benzyl group, wherein the compound is 1-(3,5-dibenzyloxyphenyl)-2-(4-benzyloxyphenyl)ethanol.

21. Compound of formula (VII)

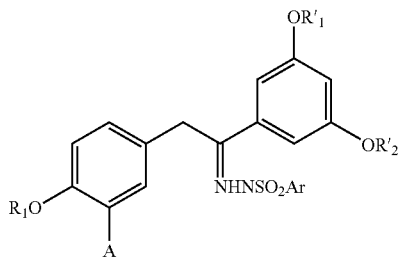

(VII)

in which

Ar represents a p-tolyl group, and

A represents hydrogen and the $R_1$, $R'_1$ and $R'_2$ groups represent methyl groups or benzyl groups, or A represents an —$OCH_3$ group and the $R_1$, $R'_1$ and $R'_2$ groups represent a methyl group, or A represents hydrogen, $R'_1$ and $R'_2$ represent a methyl group and $R_1$ represents an isopropyl group, or A represents an —$OR_2$ group, $R'_1$ and $R'_2$ represent a methyl group and $R_1$ and $R_2$ form a hydrocarbon chain of structure —$(CH_2)_n$— with n=1.

22. The process of claim 1, further comprising deprotecting the (E)-stilbene derivative of formula (VI) to provide a polyhydroxystilbene compound.

23. The process of claim 22, wherein the polyhydroxystilbene compound is resveratrol or piceatannol.

24. The process of claim 2, wherein the metal hydride is sodium borohydride.

* * * * *